United States Patent
Tsou et al.

(10) Patent No.: US 10,049,271 B2
(45) Date of Patent: Aug. 14, 2018

(54) AUTHENTICATION SYSTEM CONTROLLED BY EYE OPEN AND EYE CLOSED STATE, HANDHELD CONTROL APPARATUS THEREOF AND COMPUTER READABLE RECORDING MEDIA

(71) Applicant: UTECHZONE CO., LTD., New Taipei (TW)

(72) Inventors: Chia-Chun Tsou, New Taipei (TW); Chia-We Hsu, New Taipei (TW)

(73) Assignee: UTECHZONE CO., LTD., New Taipei (TW)

( * ) Notice: Subject to any disclaimer, the term of this patent is extended or adjusted under 35 U.S.C. 154(b) by 227 days.

(21) Appl. No.: 14/510,131

(22) Filed: Oct. 9, 2014

(65) Prior Publication Data
US 2015/0186720 A1 Jul. 2, 2015

(30) Foreign Application Priority Data

Dec. 27, 2013 (TW) .............................. 102148804 A
Feb. 25, 2014 (TW) .............................. 103106219 A

(51) Int. Cl.
*G06K 9/00* (2006.01)
*A61B 5/117* (2016.01)
(Continued)

(52) U.S. Cl.
CPC .......... *G06K 9/00597* (2013.01); *A61B 5/117* (2013.01); *A61B 5/1171* (2016.02);
(Continued)

(58) Field of Classification Search
CPC ... G06K 9/00597; A61B 5/117; A61B 5/6898; A61B 2576/02; A61B 5/6821;
(Continued)

(56) References Cited

U.S. PATENT DOCUMENTS 6,931,538 B1 *  8/2005  Sawaguchi ............ B60R 25/24
                                                 340/426.18
8,963,806 B1 *  2/2015  Starner ............ G02B 27/0093
                                                       345/7
(Continued)

FOREIGN PATENT DOCUMENTS

JP    H07313459    12/1995
JP    2001325434   11/2001
(Continued)

OTHER PUBLICATIONS

"JP 2001-325434 Translation".*
(Continued)

*Primary Examiner* — Zhihan Zhou
(74) *Attorney, Agent, or Firm* — JCIPRNET

(57) ABSTRACT

An authentication system controlled by eye open and eye closed state and a handheld control apparatus thereof are provided. The handheld control apparatus includes a housing case, an image capturing unit and a processing unit. The housing case has a window and is suitable for a user to hold. The image capturing unit is disposed in the housing case and captures an eye area of the user through the window to obtain an image sequence. The processing unit is coupled to the image capturing unit and analyzes the image sequence to obtain eye image information of the eye area of the user. The processing unit detects an eye-open state and an eye-closed state of the user based on the eye image information, converts a plurality of the eye-open states and the eye-closed states into a blink code, and accordingly generates a control command to control a security equipment.

19 Claims, 23 Drawing Sheets

(51) Int. Cl.
*A61B 5/1171* (2016.01)
*G06F 3/00* (2006.01)
*G06F 21/30* (2013.01)
*G06F 21/32* (2013.01)
*A61B 5/00* (2006.01)
*G07C 9/00* (2006.01)

(52) U.S. Cl.
CPC .............. *A61B 5/6821* (2013.01); *G06F 3/00* (2013.01); *G06F 21/30* (2013.01); *G06F 21/32* (2013.01); *G07C 9/00142* (2013.01); *A61B 5/6898* (2013.01); *A61B 2576/02* (2013.01); *G07C 9/00158* (2013.01)

(58) Field of Classification Search
CPC . G06F 21/32; G06F 3/00; G06F 21/30; G07C 9/00142; G07C 9/00158
USPC .......................................................... 348/78
See application file for complete search history.

(56) References Cited

U.S. PATENT DOCUMENTS

| | | | | |
|---|---|---|---|---|
| 2003/0194112 | A1* | 10/2003 | Lee ..................... | G06F 3/03543 382/117 |
| 2006/0072793 | A1* | 4/2006 | Determan .......... | G06K 9/00335 382/117 |
| 2009/0219405 | A1* | 9/2009 | Kaneda ................. | H04N 5/232 348/222.1 |
| 2012/0002075 | A1* | 1/2012 | Yoshizumi ........... | H04N 5/2251 348/229.1 |
| 2012/0300086 | A1* | 11/2012 | Miyashita .......... | G06K 9/00597 348/207.1 |
| 2013/0208103 | A1* | 8/2013 | Sands .................... | G06F 21/31 348/78 |
| 2014/0165187 | A1* | 6/2014 | Daesung ............ | G06K 9/00335 726/19 |

FOREIGN PATENT DOCUMENTS

| | | |
|---|---|---|
| JP | 2004211541 | 7/2004 |
| JP | 2006004294 | 1/2006 |
| JP | 2012247888 | 12/2012 |
| JP | 2013061508 | 4/2013 |
| TW | 200947262 | 11/2009 |
| TW | 201124917 | 7/2011 |
| TW | 201350081 | 12/2013 |

OTHER PUBLICATIONS

Chau et al. Real Time Eye Tracking and Blink Detection with USB Cameras. Boston University Computer Science Technical Report No. 2005-12, 2005, pp. 1-10.*
"Office Action of Japan Counterpart Application", dated Dec. 8, 2015, p. 1-p. 5.
"Office Action of Taiwan Counterpart Application" , dated Jun. 3, 2015, p. 1-p. 4.

* cited by examiner

AUTHENTICATION SYSTEM CONTROLLED BY EYE OPEN AND EYE CLOSED STATE, HANDHELD CONTROL APPARATUS THEREOF AND COMPUTER READABLE RECORDING MEDIA

CROSS-REFERENCE TO RELATED APPLICATION

This application claims the priority benefits of Taiwan application serial no. 102148804, filed on Dec. 27, 2013, and Taiwan application serial no. 103106219, filed on Feb. 25, 2014. The entirety of each of the above-mentioned patent applications is hereby incorporated by reference herein and made a part of specification.

BACKGROUND

Field of the Invention

The invention is directed to an authentication system and more particularly, to an authentication system controlled by eye open and eye close state and a handheld control apparatus thereof.

Description of Related Art

In currently available password inputting methods for safety deposit boxes, digits, texts or symbols served as passwords are inputted in to an apparatus or a machine by using keyboards. If the inputted characters match a preset password, an authentication process is passed and then a safety deposit box is opened.

However, if a password is peeped by someone else during the inputting process, the password is in a risk of being leaked, or the password might be pirated or reproduced by detecting a fingerprint or temperature remained on the keyboard. Even in advanced iris recognition, it is also incapable of ensuring that the password is inputted by a user under free will. Likewise, in an apparatus using palmprint or fingerprint recognition, palmprints and fingerprints are also reproducible, and thus, whether the user inputs the password under his/her free will can not be ensured.

SUMMARY

The invention provides an authentication system controlled by eye open and closed state and a handheld control apparatus thereof, by which an eye open and closed state made by a user may be detected for unlocking a locked state of a security equipment.

A handheld control apparatus of the invention is coupled to a security equipment and performs an authentication for a user. The handheld control apparatus includes a housing case, an image capturing unit and a processing unit. The housing case has a window. The image capturing unit is disposed within the housing case to capture an eye area of the user through the window to obtain an image sequence. The processing unit is coupled to the image capturing unit and analyzes the image sequence to obtain eye image information of the eye area of the user. The processing unit detects an eye-open state and an eye-closed state of the user based on the eye image information, converts a plurality of the eye-open states and the eye-closed states into a blink code, and accordingly generates a control command to control a security equipment.

In an embodiment of the invention, the handheld control apparatus based on eye open and closed state further includes a light source, a display unit and a reflective mirror. The light source is disposed in the housing case, and adjacent to the window. The display unit is disposed in the housing case, and configured to display operating information. The reflective mirror is disposed in the housing case, and reflects an image of the operating information to the window.

In an embodiment of the invention, the security equipment includes a safety deposit box, an access control system or a network authentication system.

In an embodiment of the invention, the handheld control apparatus based on eye open and closed state further includes a wireless transmission module. The wireless transmission module is configured to wirelessly transmit the control command to the security equipment.

In an embodiment of the invention, when the processing unit determines that the blink code matches a preset unlock password, a lock of the security equipment unlocks a locked state. In an embodiment of the invention, when the processing unit determines that the blink code does not match the preset unlock password, the lock of the security equipment is maintained in the locked state.

In an embodiment of the invention, the processing unit searches an eye object in the eye area based on the eye image information, and determines whether the eye area is in the eye-open state or the eye-closed state according to a size of the eye object.

In an embodiment of the invention, the processing unit determines that the eye area is under the eye-closed state when the height of the eye object is less than a height threshold and the width of the eye object is greater than a width threshold. The processing unit determines that the eye area is under the eye-open state when the height of the eye object is greater than or equal to the height threshold or the width of the eye object is less than or equal to the width threshold.

In an embodiment of the invention, after the eye object is searched, the processing unit recognizes biometric information of the eye object, wherein when the biometric information matches preset user information, the processing unit determines whether the eye area is under the eye-open state or the eye-closed state according to the size of the eye object.

In an embodiment of the invention, the processing unit detects the state of the eye area within a unit time. When the processing unit detects that the eye area is under the eye-open state within the unit time, the processing unit generates a first code. When the processing unit detects that the eye area is in the eye-closed state within the unit time, the processing unit generates a second code. The processing unit permutes a plurality of the first codes and the second codes generated based on the plurality of the eye-open states and the eye-closed states within a preset time in sequence to form the blink code.

In an embodiment of the invention, the processing unit compares the blink code with each bit of the preset unlock password. When each bit of the blink code matches the preset unlock password, the processing unit determines that the blink code matches the preset unlock password. When at least one bit in the blink code does not match the preset unlock password, the processing unit determines that the blink code does not match the preset unlock password.

In an embodiment of the invention, the processing unit defines the continuously generated first and second codes as a blink code. The processing unit counts a blink number of the blink code, and compares the blink number with a preset blink number. When the blink number is equal to the preset blink number, the processing unit determines that the blink code matches the preset unlock password. When the blink number is unequal to the preset blink number, the processing unit determines that the blink code does not match the preset unlock password.

In an embodiment of the invention, the processing unit defines the continuously generated first and second codes as a blink code. The processing unit calculates a blink frequency of the blink code, and determines whether the blink frequency is within a preset blink frequency range. When the blink frequency is within the preset blink frequency range, the processing unit determines that the blink code matches the preset unlock password. When the blink frequency is beyond the preset blink frequency range, the processing unit determines that the blink code does not match the preset unlock password.

In an embodiment of the invention, the processing unit calculates a persistently eye-open time of the first code continuously appearing in the blink code, and determines whether the persistently eye-open time is within a preset eye-open time range. When the persistently eye-open time is within the preset eye-open time range, the processing unit determines that the blink code matches the preset unlock password. When the persistently eye-open time is beyond the preset eye-open time range, the processing unit determines that the blink code does not match the preset unlock password.

In an embodiment of the invention, the processing unit calculates a persistently eye-closed time of the second code continuously appearing in the blink code, and determines whether the persistently eye-closed time is within a preset eye-closed time range. When the persistently eye-closed time is within the preset eye-closed time range, the processing unit determines that the blink code matches the preset unlock password. When the persistently eye-closed time is beyond the preset eye-closed time range, the processing unit determines that the blink code does not match the preset unlock password.

In an embodiment of the invention, the processing unit further determines whether the blink code matches an emergent SOS password. When the blink code matches the emergent SOS password, the processing unit sends out an emergent SOS message.

An authentication system includes a handheld control apparatus, a processing unit and a security equipment. The handheld control apparatus is configured to capture an eye area of a user to obtain an image sequence. The processing unit receives and analyzes the image sequence from the handheld control apparatus through a data transmission interface to obtain eye image information of the eye area in the image sequence. The security equipment is coupled to the processing unit for switching a locked state according to a control command. The processing unit detects an eye-open state and an eye-closed state of the user based on the eye image information, converts a plurality of the eye-open states and the eye-closed states into a blink code, and accordingly generates the control command.

In an embodiment of the invention, the data transmission interface includes a wireless transmission module.

A computer readable recording media stores a program which executes an authentication method for a user by a handheld control apparatus coupled to a security equipment. The handheld control apparatus includes a housing case and an image capturing unit. The authentication method includes following steps: capturing, by the image capturing unit, an eye area of the user through a window of the housing case to obtain an image sequence; analyzing the image sequence to obtain eye image information of the eye area in the image sequence; detecting an eye-open state and an eye-closed state of the user based on the eye image information; and, converting a plurality of the eye-open states and the eye-closed states into a blink code, and accordingly generating a control command to control the security equipment.

Based on above, the authentication system controlled by eye open and eye closed state and the handheld control apparatus thereof are provided according to the embodiments of the invention. The authentication system may utilize a specific eye movements (e.g., blinking, persistently eye-opening and/or persistently eye-closing) as the unlock password for unlocking the locked state of the lock. Due to the eye movements of the user being difficulty peeped or observed by others, security equipments (e.g., access control systems or safety deposit boxes) applying the authentication system can be significantly advanced in security, and passwords therefore can be prevented from being leaked.

To make the above features and advantages of the disclosure more comprehensible, several embodiments accompanied with drawings are described in detail as follows.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
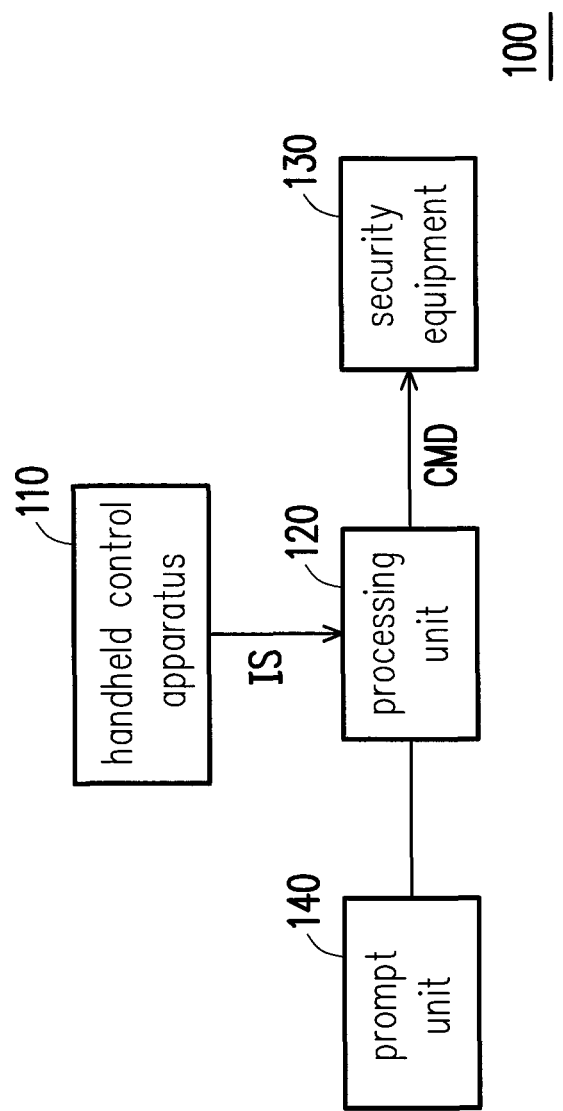
FIG. 1 is a schematic diagram illustrating functional blocks of an authentication system controlled by eye open and eye closed state according to an embodiment of the invention.

In order to make content of the present disclosure more comprehensible, embodiments are described below as the examples to prove that the present disclosure can actually be realized. Herein, elements/components/steps with same reference numerals represent same or similar parts in the drawings and embodiments. Moreover, terms that indicate directions, such as "above", "below", "left" and "right" in the following embodiments are used in reference to directions in the accompanying drawings and are hence used for description but not for limiting the disclosure.

FIG. 1 is a schematic diagram illustrating functional blocks of an authentication system controlled by eye open and eye closed state according to an embodiment of the invention. Referring to FIG. 1, an authentication system 100 controlled by eye open and eye closed state includes a handheld control apparatus 110, a processing unit 120 and a security equipment 130.

In the present embodiment, the handheld control apparatus 110 is movably coupled to the security equipment 130. The handheld control apparatus 110 is configured to capture an eye area of a user to obtain an image sequence IS (i.e., a plurality of continuously captured images) to be provided to the processing unit 120. The processing unit 120 is coupled to the handheld control apparatus 110. The processing unit 120 performs image process and analysis on the image sequence IS captured by the handheld control apparatus 110, so as to obtain eye image information of the eye area of the user in the image sequence IS.

Accordingly, the processing unit 120 may determine an eye open and eye closed state (including an eye-open state and an eye-closed state) of the user according to the eye image information, and then determine whether the eye-open state or the eye-closed state of the user matches a preset unlock password (which may be stored in a storage unit (not illustrated)). The processing unit 120 decides whether to send out a corresponding control command CMD according to a determination result, so as to switch a configuration state of the security equipment 130 to be a locked state or an unlocked state. That is, the security equipment 130 may be in the locked state or the unlocked state in response to the control command CMD of the processing unit 120. In the present embodiment, the processing unit 120 is, for example, a device such as a central processing unit (CPU), a graphics processing unit (GPU), or other programmable microprocessor; and the security equipment 130 may be a safety deposit box, an access control system or a network authentication system. In addition, the processing unit 120 may be disposed in the handheld control apparatus 110 or the security equipment 130 (which will be described later in subsequent embodiments) based on design requirements, which are not particularly limited in the invention.

Additionally, in the authentication system 100 of the present embodiment, a prompt unit 140 may be optionally disposed. The prompt unit 140 may be configured to prompt a current configuration state of the security equipment 130, such as prompting whether the security equipment 130 is in the locked state or the unlocked state. Herein, the prompt unit 140 may prompt the user with the current state of the security equipment 130 by means of text indication, light signal indication or any other available indication, but the invention is not limited thereto.

Figure 2:
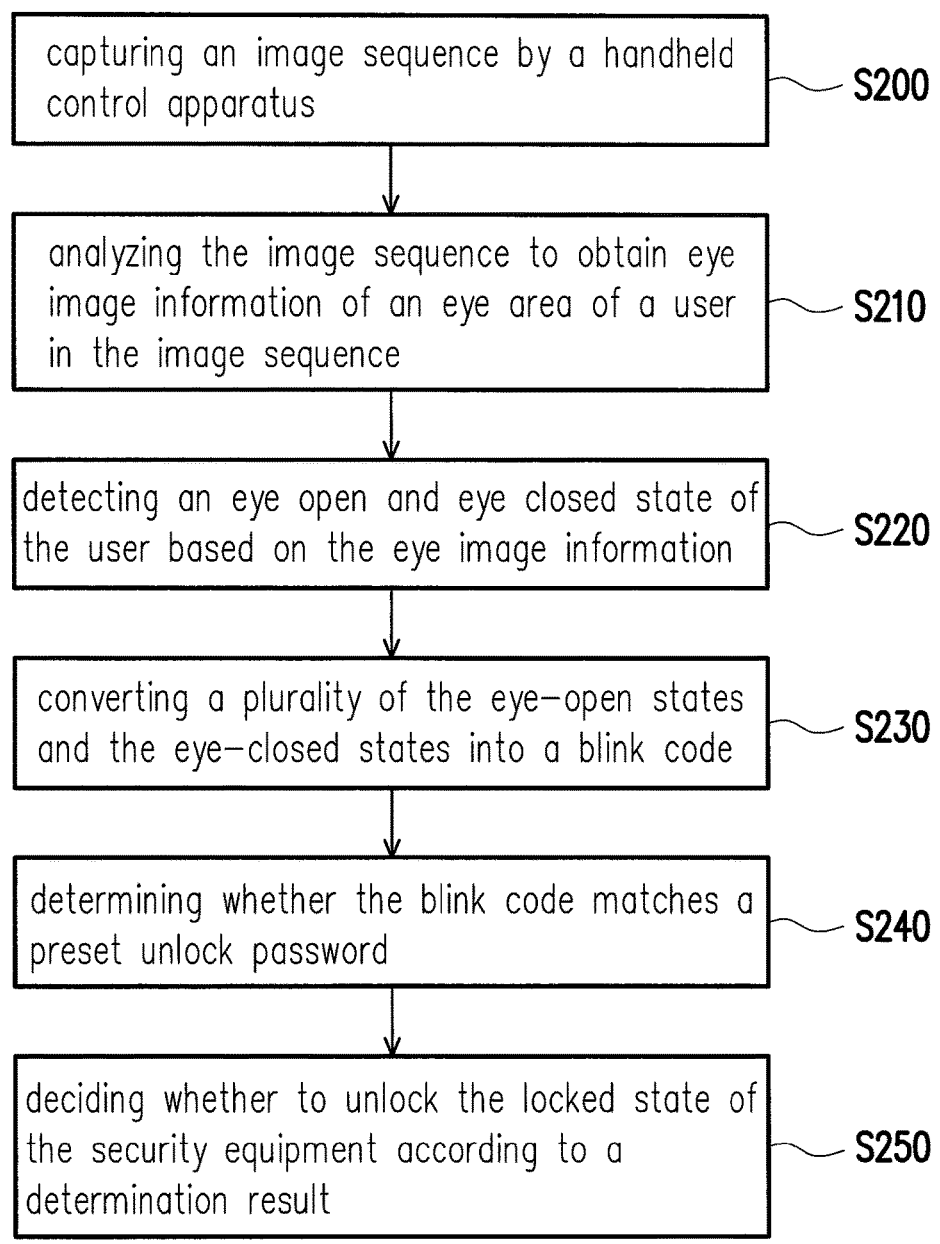
FIG. 2 is a flowchart illustrating a password inputting method based on eye open and closed state according to an embodiment of the invention.

The authentication system may perform an operation of deciding whether to unlock the locked state of the security equipment 130 based on an eye open and closed state of the user according to the process flow illustrated in FIG. 2.

FIG. 2 is a flowchart illustrating a password inputting method based on eye open and closed state according to an embodiment of the invention. Referring to FIG. 1 and FIG. 2, first, the handheld control apparatus 110 captures an image sequence IS (step S200). Then, the processing unit 120 analyzes the image sequence IS to obtain eye image information of an eye area of a user in the image sequence IS (step S210). Thereafter, the processing unit 120 detects an eye open and eye closed state (including an eye-open state and an eye-closed state) of the user based on the eye image information (step S220).

After the eye open and eye closed state of the user is detected, the processing unit 120 converts a plurality of the detected eye-open states and the detected eye-closed states into a blink code (step S230) and determines whether the blink code matches a preset unlock password (step S240). Herein, the preset unlock password may be, for example, conditions such as a number of blinks, a frequency of the blinks and/or a duration of eye open or eye closed (which will be described later in subsequent embodiments). Thereby, the processing unit 120 may decide whether to unlock the locked state of the security equipment 130 according to a determination result of above determination (step S250).

Figure 3:
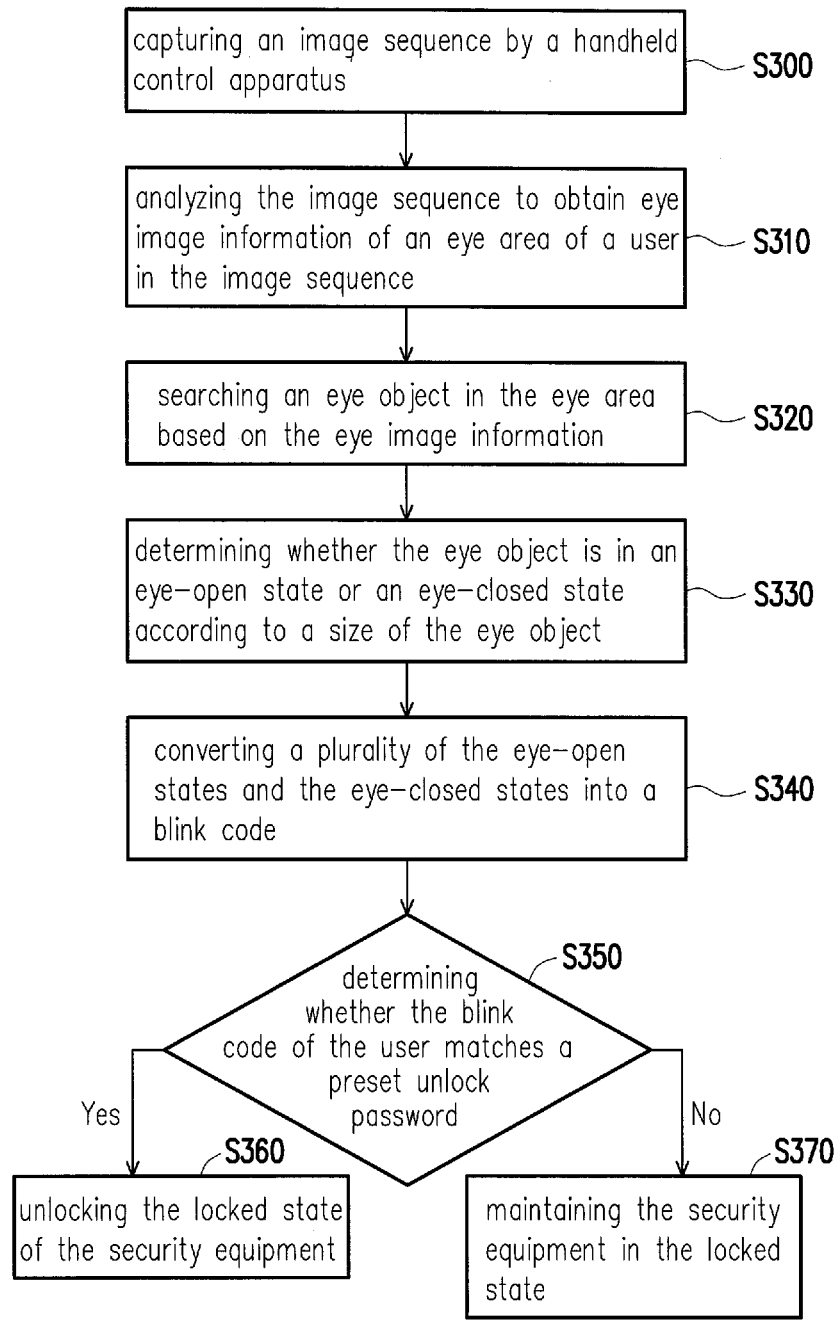
FIG. 3 is a flowchart illustrating a password inputting method based on eye open and closed state according to another embodiment of the invention.

A specific process flow for unlocking according to the eye open and closed state will be further described with reference to the embodiment of FIG. 3 below. FIG. 3 is a flowchart illustrating a password inputting method based on eye open and closed state according to another embodiment of the invention. Herein, the following embodiments are described along with the authentication system 100 of the embodiment illustrated in FIG. 1, but the password inputting method based on the eye open and closed state may be applicable to any type of hardware structure of the security apparatus and the invention is not limited thereto.

First, referring to FIG. 3, in the password inputting method of the present embodiment, the handheld control apparatus 110 similarly captures an image sequence IS (step S300), such that the processing unit 120 may analyze the image sequence IS to obtain eye image information of an eye area of a user in the image sequence (step S310).

Then, the processing unit 120 searches an eye object in the eye area based on the eye image information (step S320) and determines whether the eye object is in an eye-open state or an eye-closed state according to a size of the eye object (step S330). Thereafter, the processing unit 120 detects an eye open and closed state of the user within a unit time according to the eye-open/eye-closed state of the eye object, so as to convert a plurality of eye-open states and a plurality of eye-closed states into a blink code (step S340).

After the blink code of the user is obtained, the processing unit 120 compares the obtained blink code with a preset unlock password to determine whether the blink code of the user matches the preset unlock password (step S350). Under a condition that the security equipment 130 is in the locked state, if the determination result of step S350 is yes, the processing unit 120 unlocks the locked state of the security equipment 130 (i.e., the security equipment 130 is switched to the unlocked state) (step S360). In contrary, if the determination result is no, the processing unit 120 maintains the security equipment 130 in the locked state (step S370). From another aspect, if the security equipment 130 is in the unlocked state, regardless of whether the determination result of step 350 is yes, the security equipment 130 is maintained in the unlocked state. It is worth mentioning that, in an exemplary embodiment, when the security equipment 130 is in the unlocked state, the user may make a set of continuous blinks and define the preset unlock password by utilizing the blink code corresponding to the continuous blinks. Naturally, the preset unlock password may also be preset by the designer and stored in the storage unit (not illustrated) of the authentication system 100 (e.g., storage box), but the invention is not limited thereto.

It is worth mentioning that, in an exemplary embodiment, after the eye object is searched (step S320), biometric information (e.g., iris or retinal information) of the eye object of the user may be recognized in advance so as to confirm the user's identity. Follow-up steps S330 to S370 would be further performed only if the user's identity is correct. Otherwise, follow-up steps for identifying eye movements are stopped/refused.

FIG. 4A, FIG. 5, FIG. 6A to FIG. 6E and FIG. 7A to FIG. 7E illustrate examples of specific flows respectively for performing step S330 of identifying the state of the eye object, performing step 340 of converting into the blink code and step S350 of determining whether the eye open and closed state matches the preset unlock password.

Figure 4A:
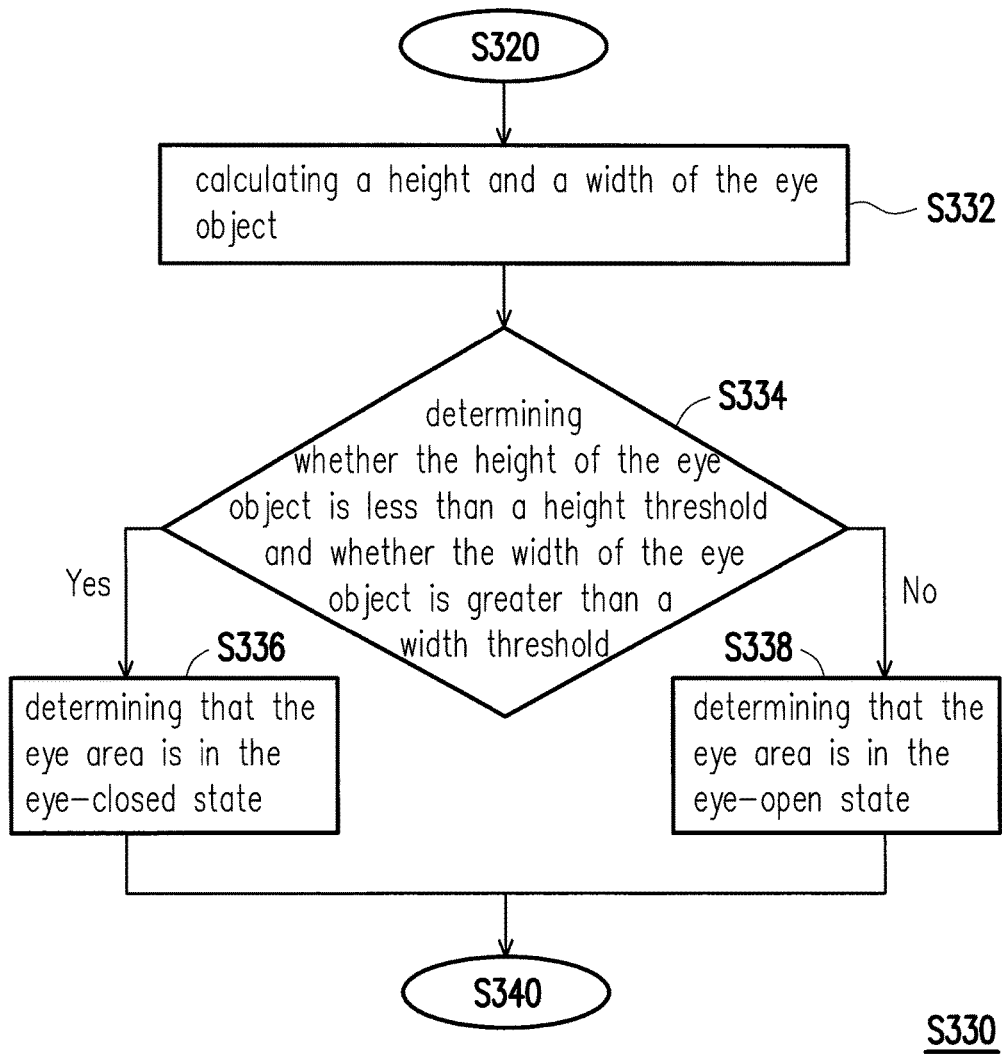
FIG. 4A is a flowchart illustrating the step of determining the state of the eye area according to an embodiment of FIG. 3.
Figure 4B:
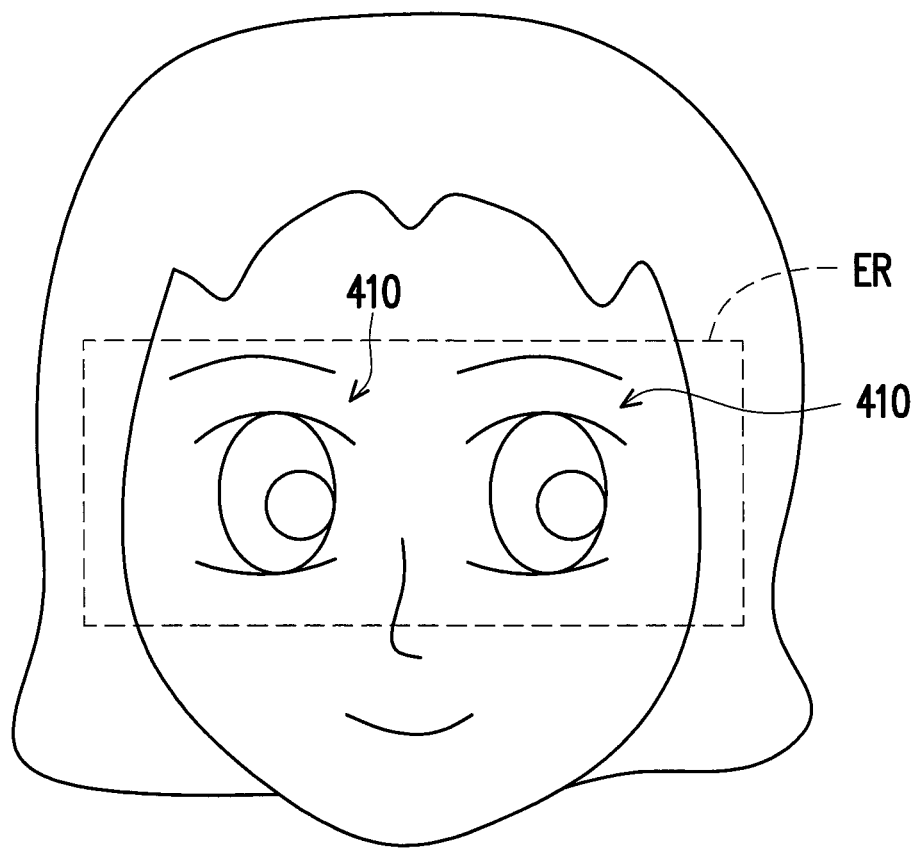
FIG. 4B and FIG. 4C are schematic diagrams illustrating the step of determining the state of the eye area according to one of the embodiments of FIG. 3.
Figure 4C:
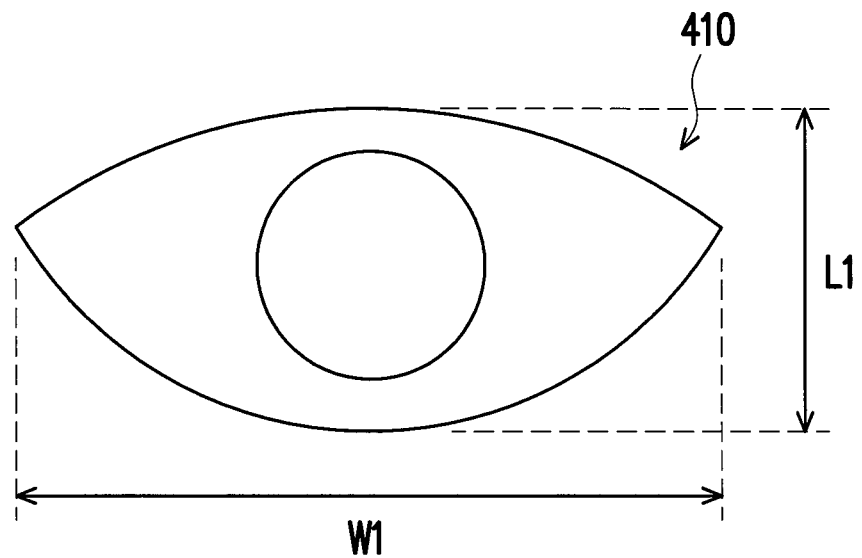
Figure 4C:
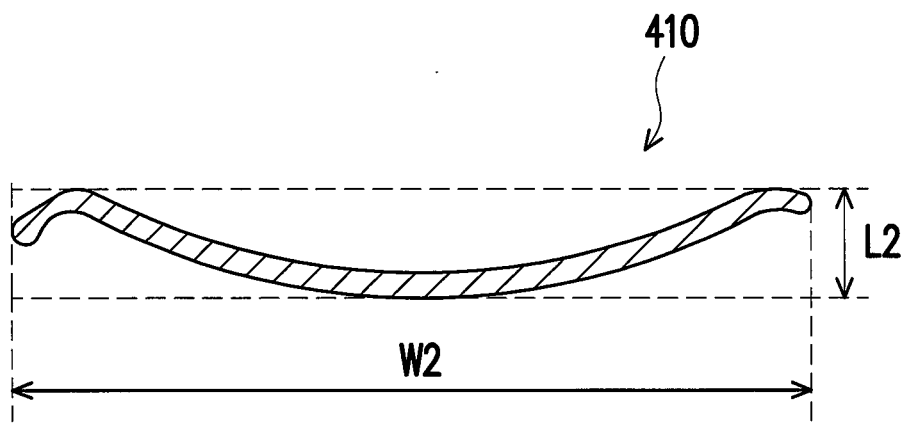

FIG. 4A is a flowchart illustrating the step of determining the state of the eye area according to an embodiment of FIG. 3. FIG. 4B and FIG. 4C are schematic diagrams illustrating the step of determining the state of the eye area according to one of the embodiments of FIG. 3. Referring to FIG. 4A to FIG. 4C together, after an eye object 410 in an eye area ER is searched by the processing unit 120, the processing unit 120 performs image process on the eye image information to obtain image information that clearly indicates borders of the eye object, such that the processing unit 120 may calculate a dimension (including a height and a width) of the eye object 410 according to the image information (step S332).

For instance, the processing unit 120 may obtain an enhanced image by adjusting a contrast (e.g., a gain and an offset) of the eye image information and then sequentially perform denoising, edge sharpening, binarization processing, edge sharpening again, etc. on the enhanced image to obtain an image of the eye object 410 shown in FIG. 4B.

After detecting the eye object 410 and calculating the size of the eye object 410, the processing unit 120 determines whether the height of the eye object 410 is less than a height threshold (for example, the height threshold ranges from 15 to 17 pixels) and whether the width of the eye object 410 is greater than a width threshold (for example, the width threshold ranges from 70 to 90 pixels) according to the size of the eye object 410 (step S334). When detecting that the height of the eye object 410 is less than the height threshold, and the width of the eye object 410 is greater than the width threshold, the processing unit 120 determines that the eye area ER is now in the eye-closed state (as shown in the lower part of FIG. 4C) (step S336). On the other hand, if detecting that the eye object 410 does not satisfy at least one of the aforementioned conditions, the processing unit 120 determines that the eye area ER is now under the eye-open state (as shown in the upper part of FIG. 4C) (step S338).

Referring to FIG. 4C, the height of the eye object 410 may be, for example, a distance (e.g., the height L1 or L2) from the top vertex of the orbital border to the bottom vertex of the orbital border, while the width may be, for example, a distance (e.g., the width W1 or W2) from the left vertex of the orbital border to the right vertex of the orbital border, which construe no limitations to the invention. In other embodiments, the processing unit 120 may also calculate the height and the width according to user-defined characteristic points on the eye object 410.

Moreover, it should be mentioned that in the present embodiment, even though whether the eye area ER is under the eye-open state or the eye-closed state is determined based on one eye, the invention is not limited thereto. In other embodiments, the eye-open/eye-closed state of the eye area ER may be determined based on both eyes (e.g., the eye area ER is determined to be in the eye-closed state only when detecting that both eyes are closed). Alternatively, the eye-open/eye-closed state corresponding to the left eye area (e.g., the left half of the eye area ER) and the eye-open/eye-closed state corresponding to the right eye area (e.g., the right half of the eye area ER) may be independently defined according to images of the left and the right eyes.

Figure 5:
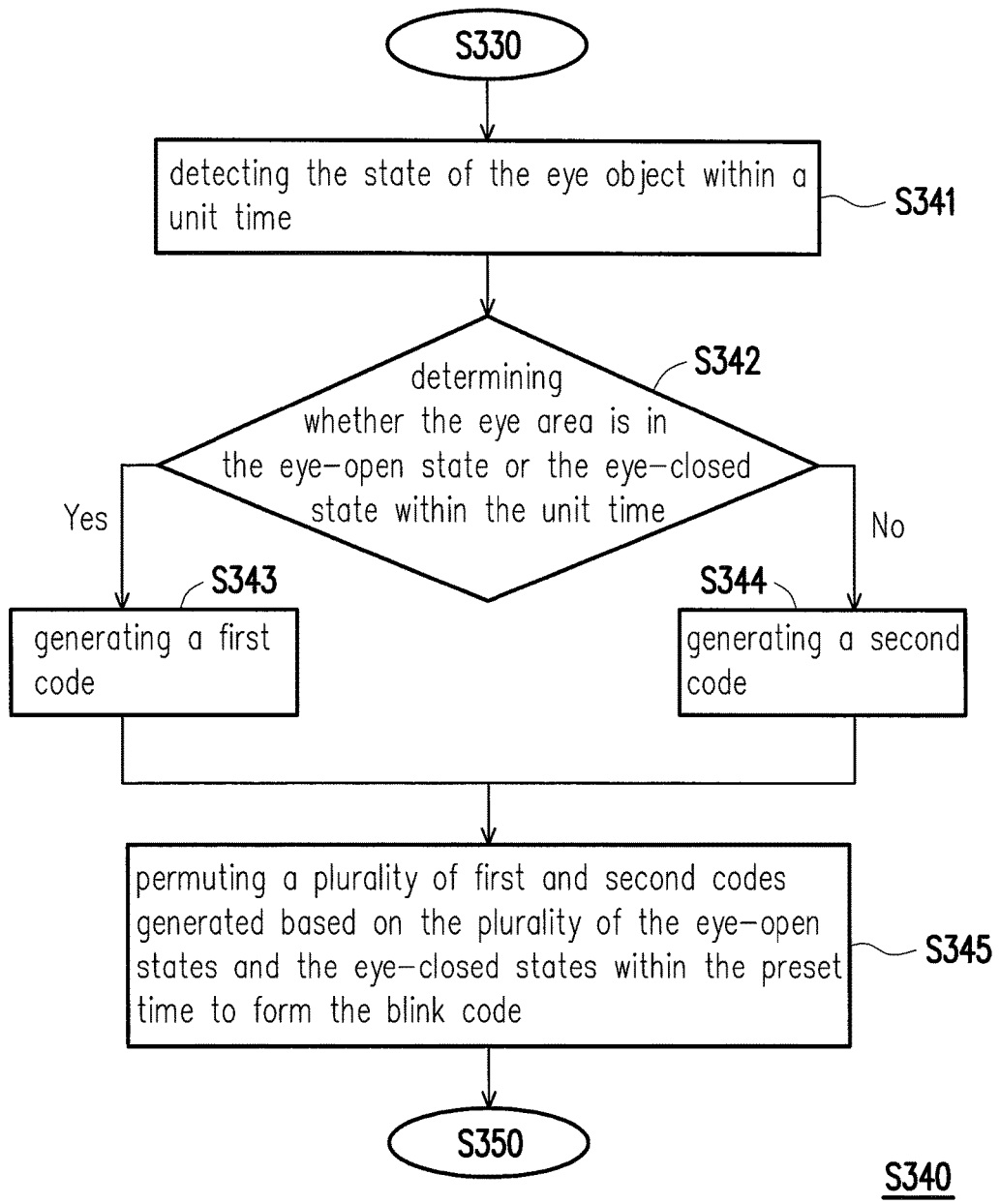
FIG. 5 is a flowchart illustrating the step of converting the eye-open states and the eye-closed states into a blink code according to one of the embodiments of FIG. 3.

After determining that the eye object is in the eye-open state or in the eye-closed state, the processing unit 120 may perform step S340 of converting into the blink code according to the process flow illustrated in FIG. 5.

FIG. 5 is a flowchart illustrating the step of converting the eye-open states and the eye-closed states into the blink code according to one of the embodiments of FIG. 3. Referring to FIG. 5, after determining the eye area is in the eye-open state or in the eye-closed state, the processing unit 120 further detects the state of the eye object within a unit time (which may be defined by the designer) (step S341) and determines whether the eye area is either in the eye-open state or the eye-closed state within the unit time (step S342). If it is determined that the eye area is under the eye-open state within the unit time in step S342, the processing unit 120 determines that the user makes an eye opening action so as to generate a first code (step S343). On the other hand, if it is determined that the eye area is in the eye-closed state within the unit time in step S342, the processing unit 120 determines that the user makes an eye closing action so as to generate a second code (step S344). Herein, the first code may be, for example, logic "1", while the second code may be, for example, logic "0", but the invention is not limited thereto. In another embodiment, the first code corresponding to the eye-open state may also be logic "0", while the second code corresponding to the eye-closed state may also be logic "1".

The processing unit 120 continuously obtains a plurality of eye-open states and a plurality of eye-closed states of the user within a preset time (which may be considered as being consisting of a plurality of unit time) and permutes a plurality of first and second codes generated based on the plurality of the eye-open states and the eye-closed states within the preset time to form the blink code (step S345). The processing unit 120 continues to perform step S350 of comparing the blink code with the preset unlock password so as to determine whether the blink code obtained based on the eye movements of the user matches the preset unlock password. The process flows illustrated in FIG. 6A to FIG. 6E accompanying with examples of coding formats of the blink code illustrated in FIG. 7A to FIG. 7E are utilized to describe different determination manners for scenarios with different preset unlock password. FIG. 7A to FIG. 7E illustrate blink codes PUC and PUC' which are code sequences (illustrated as 12-bit code sequences for example, but the invention is not limited thereto) obtained by the processing unit 120 sequentially converting the eye-open states and eye-closed states of the eye object based on each unit time UT within a preset time PT. In the blink codes PUC and PUC', each first code B1 generated based on the eye-open state is labeled as logic "1", while each second code B2 generated by the eye-closed state is labeled as logic "0", which construe no limitations to the invention.

Figure 6A:
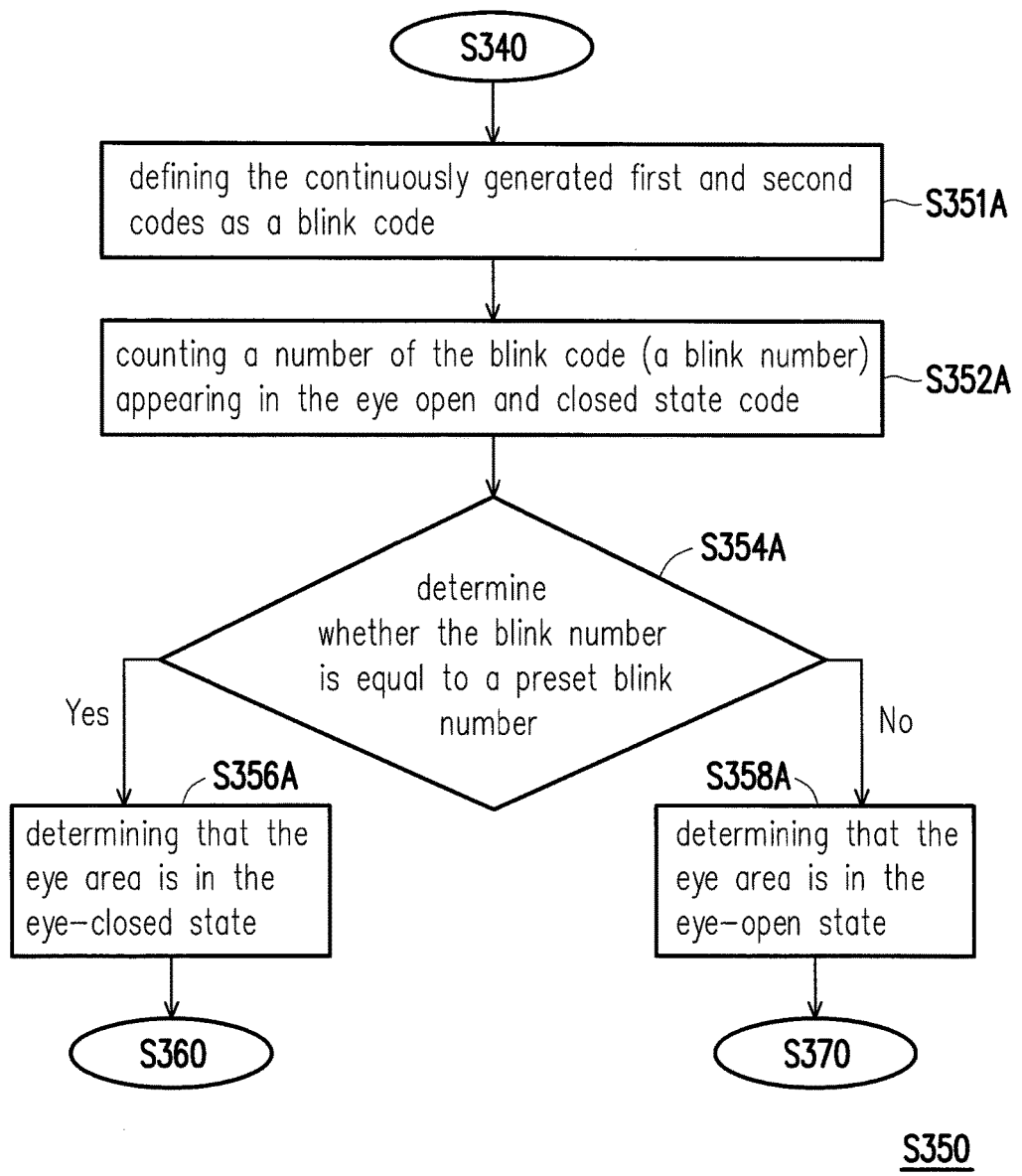
FIG. 6A to FIG. 6E are flowcharts illustrating the step of determining whether the blink code matches the preset unlock password according to different examples of the embodiment of FIG. 3.

First referring to FIG. 6A, in the present embodiment, the preset unlock password is set to be a specific blink number. Specifically, in step S350 of the present embodiment, the processing unit 120 defines the continuously generated first and second codes as a blink code (which indicates that the user blinks while the processing unit 120 continuously generates the first and second codes) (step S351A), and counts a number of the blink code (i.e., a blink number of the user) (step S352A). Then, the processing unit 120 compares the blink number with a preset blink number so as to determine whether the blink number being counted is equal to the preset blink number (step S354A). If determining that the blink number is equal to the preset blink number, the processing unit 120 determines that the blink code of the user matches the preset unlock password (step S356A) and continues to perform step S360 to unlock the locked state of the security equipment 130. Otherwise, if determining that the blink number is unequal to the preset blink number, the processing unit 120 determines that the blink code of the user does not match the preset unlock password (step S358A) and continues to perform step S370 to maintain the security equipment 130 in the locked state.

Figure 7A:
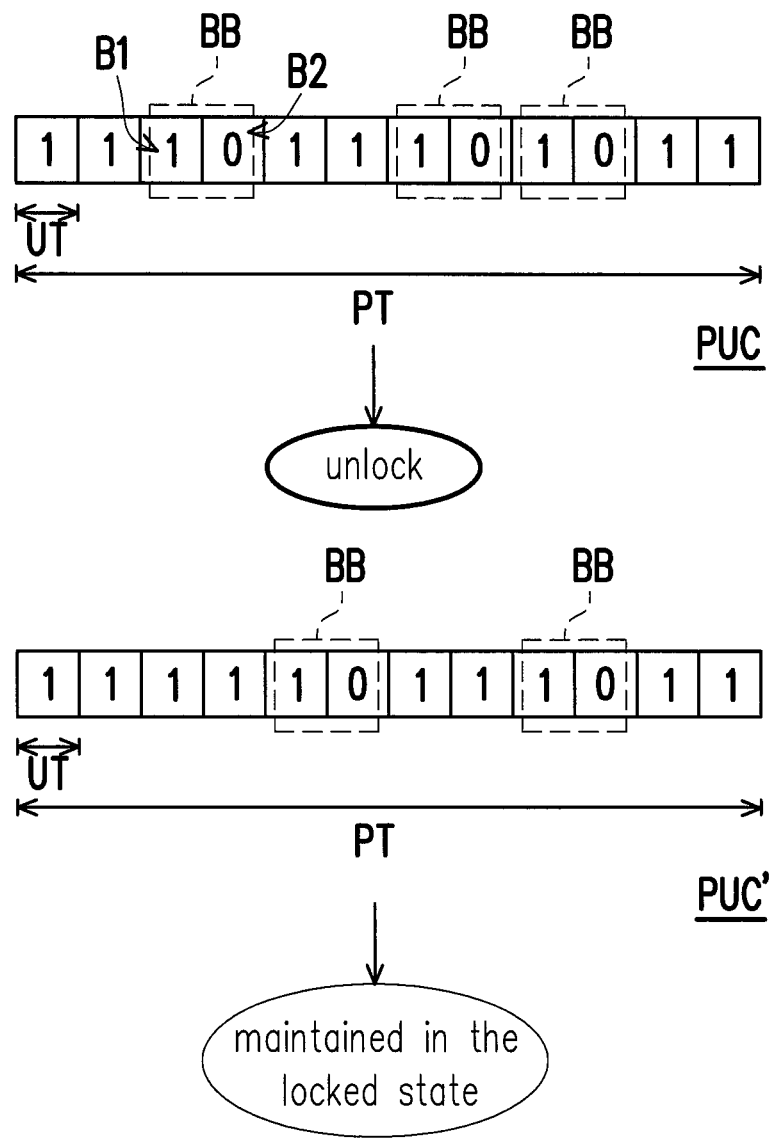
FIG. 7A to FIG. 7E are schematic diagrams illustrating coding formats of the blink code according to the different examples of FIG. 6A to FIG. 6E, respectively.

For instance, referring to FIG. 6A and FIG. 7A together, it is assumed that the preset blink number is set to be 3. When obtaining a blink code PUC formed by a code sequence of "111011101011" based on the eye movements of the user, the processing unit 120 defines a code of "10" as a blink code BB so as to count a number of the blink code BB. In the blink code PUC, the processing unit 120 counts that the blink code BB appear for 3 times (i.e., the user blinks for 3 times), and thus, determines that the blink code PUC of the user matches the preset unlock password and unlocks the locked state of the security equipment 130.

On the other hand, when obtaining a blink code PUC' formed by a code sequence of "111110111011" based on the eye movements of the user, the processing unit 120 defines a code of "10" as a blink code BB in the same way and counts a number of the blink code BB. In the blink code PUC', the processing unit 120 counts that the blink code BB appears for only twice (i.e., the user blinks for twice), and thus, determines that the blink code PUC of the user does not match the preset unlock password and maintains the security equipment 130 in the locked state.

Herein, the aforementioned preset blink number (3 times) is only an example for illustration, but construes no limitations to the invention. Furthermore, the preset blink number may be set to be N times, and the value of N may be a positive integer selected by the designer.

Figure 6B:
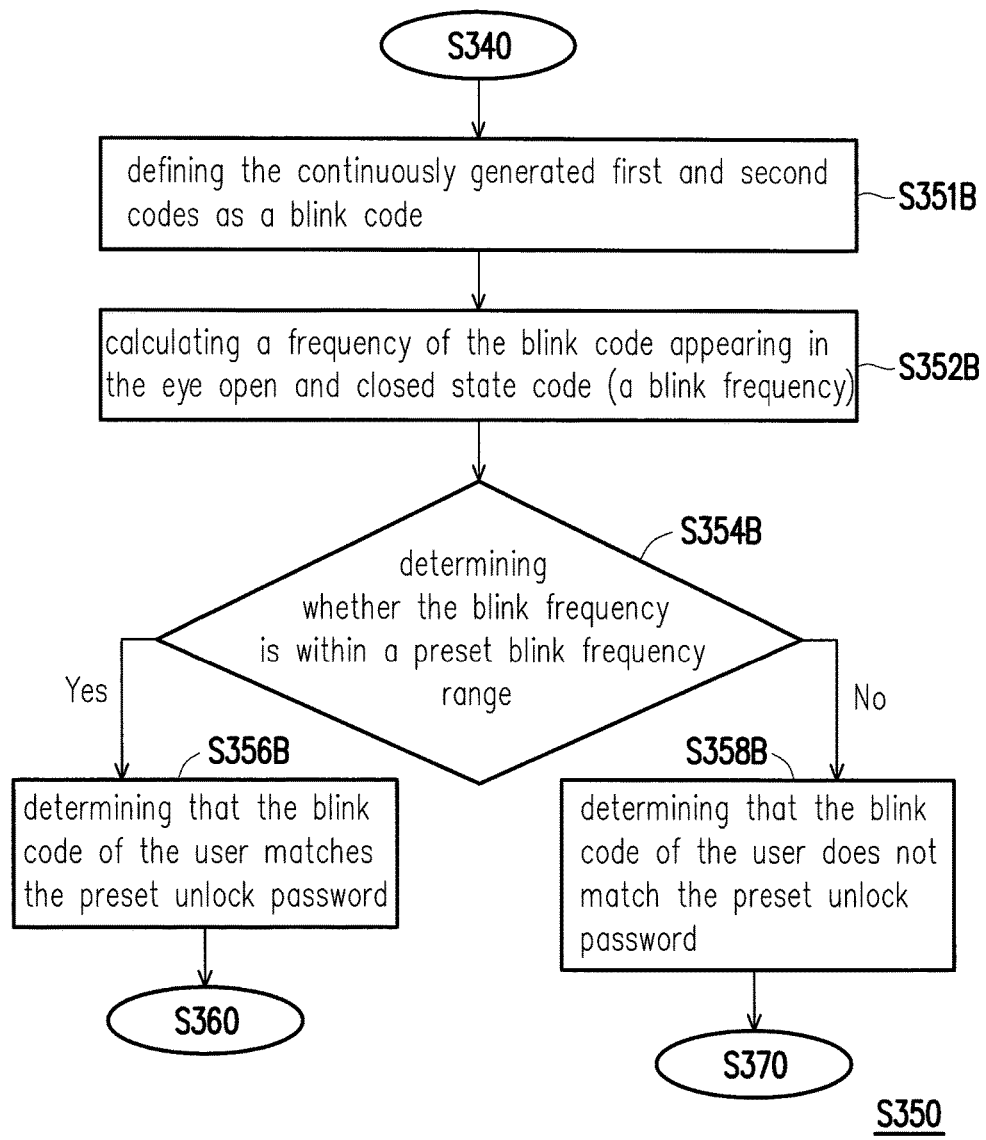

Referring to FIG. 6B, in the present embodiment, the preset unlock password is set to be a specific blink frequency range. Specifically, in step S350 of the present embodiment, the processing unit 120 defines the continuously generated first and second codes as a blink code (step S351B) and calculates a frequency of the blink code appearing in the blink code (i.e., a blink frequency of the user) (step S352B). Then, the processing unit 120 determines whether the calculated blink frequency is within a preset blink frequency range (step S354B). If determining that the blink frequency is within the preset blink frequency range, the processing unit 120 determines that the blink code of the user matches the preset unlock password (step S356B) and continues to perform step S360 to unlock the locked state of the security equipment 130. Otherwise, if determining that the blink frequency is beyond the preset blink frequency range, the processing unit 120 determines that the blink code of the user does not match the preset unlock password (step S358B) and continues to perform step S370 to maintain the security equipment 130 in the locked state.

Figure 7B:
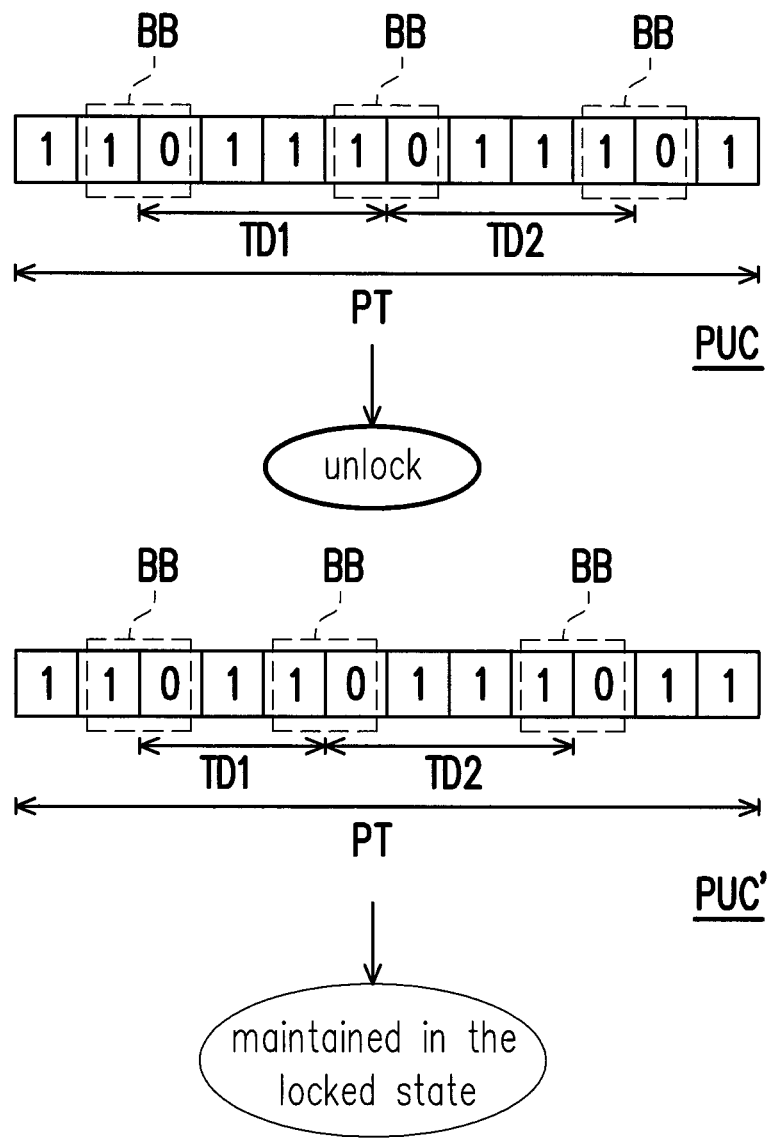

For instance, referring to FIG. 6B and FIG. 7B together, it is assumed that the preset blink frequency range is set to range from 1.9 to 2.1 seconds/blink number. When obtaining a blink code PUC formed by a code sequence of "110111011101" based on the eye movements of the user, the processing unit 120 defines a code of "10" as a blink code BB so as to calculate a frequency/time interval of the blink code BB. In the blink code PUC, the processing unit 120 calculates that a time interval between the first blink code BB and the second blink code BB is TD1, and a time interval between the second blink code BB and the third blink code BB is TD2. When the time intervals TD1 and TD2 are within a range from 1.9 to 2.1 seconds (i.e., the user blinks at a frequency of once per 1.9 to 2.1 seconds), the processing unit 120 determines that the blink code PUC of the user matches the preset unlock password and unlocks the locked state of the security equipment 130.

On the other hand, when obtaining a blink code PUC' formed by a code sequence of "110110111011" based on the eye movements of the user, the processing unit 120 defines a code of "10" as a blink code BB in the same way and calculates a frequency of the blink code BB appearing in the blink code PUC'. In the blink code PUC', the processing unit 120 calculates that a time interval between the first blink code BB and the second blink code BB is TD1', and a time interval between the second blink code BB and the third blink code BB is TD2'. When one of the time intervals TD1' and TD2' is beyond the range from 1.9 to 2.1 seconds (e.g., the time interval TD1'), the processing unit 120 determines that the blink code PUC' of the user does not match the preset unlock password and maintains the security equipment 130 in the locked state.

Herein, the preset blink frequency range (1.9 to 2.1 seconds/blink number) is only an example for illustration and construes no limitations to the invention. Furthermore, upper and lower limits of the set preset blink frequency range may be selected by the designer and may also be a specific frequency (e.g., 2 seconds/blink number).

Figure 6C:
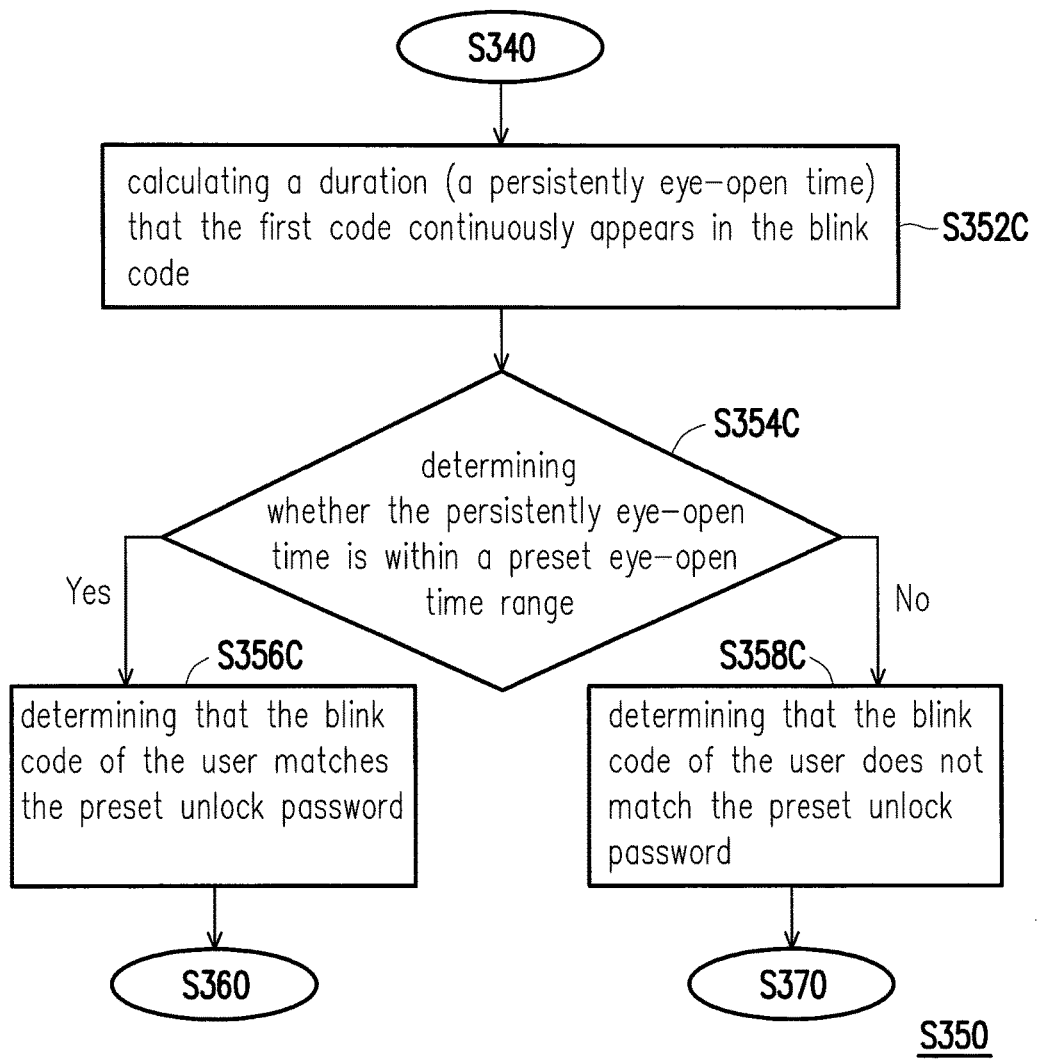

Referring to FIG. 6C, in the present embodiment, the preset unlock password is set to be a specific persistently eye-open time. Specifically, in step S350 of the present embodiment, the processing unit 120 calculates a duration (i.e., a persistently eye-open time) that the first code corresponding to the eye-open state continuously appears in the blink code (step S352C). Then, the processing unit 120 determines whether the calculated persistently eye-open time is within a preset eye-open time range (step S354C). If determining that the persistently eye-open time is within the preset eye-open time range, the processing unit 120 determines that the blink code of the user matches the preset unlock password (step S356C) and continues to perform step S360 of unlocking the located state of the security equipment 130. Otherwise, if determining that the persistently eye-open time is beyond the preset eye-open time range, the processing unit 120 determines that the blink code of the user does not match the preset unlock password (step S358C) and continues to perform step S370 to maintain the security equipment 130 in the locked state.

Figure 7C:
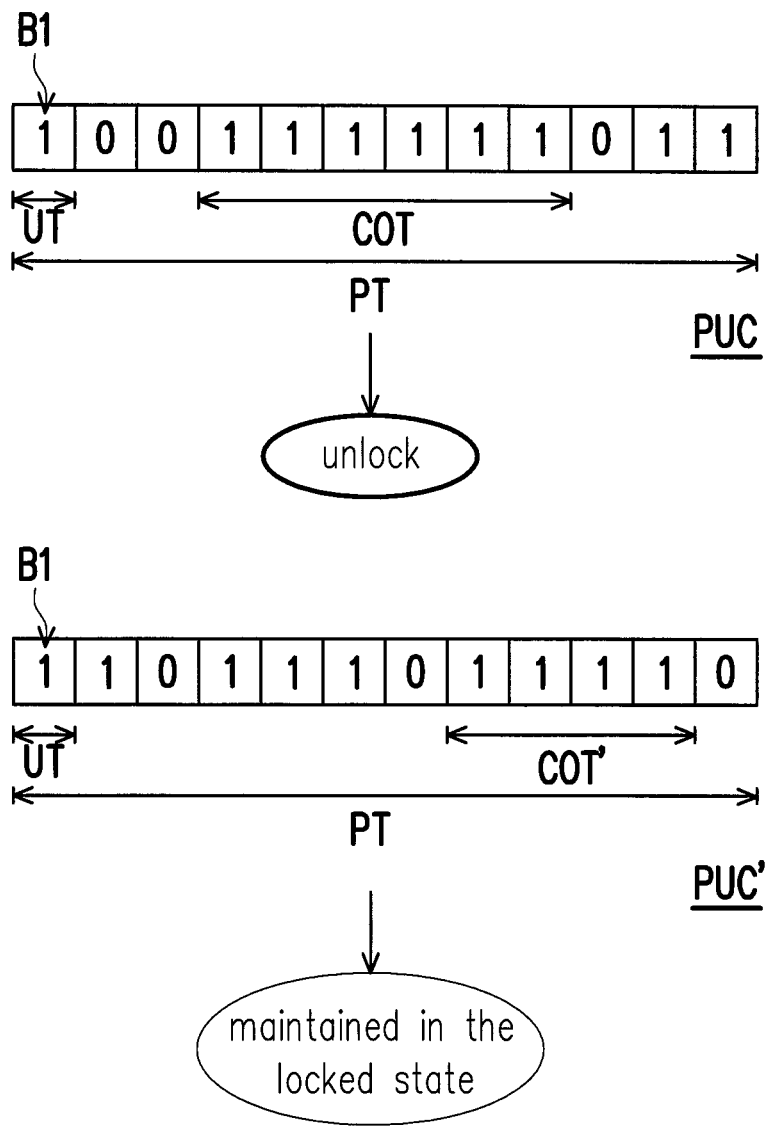

For instance, referring to FIG. 6C and FIG. 7C together, it is assumed that the preset eye-open time range is set to range from 9 to 11 seconds. When obtaining a blink code PUC formed by a code sequence of "100111111011" based on the eye movements of the user, the processing unit 120 calculates a maximum time length COT that the first code B1 (labeled as "1") continuously appears in the blink code PUC. In the blink code PUC, the processing unit 120 calculates that the maximum time length COT of the first code B1 continuously appearing is about 6 unit time UT. When determining that the maximum time length COT is within a range from 9 to 11 seconds (i.e., the user keeps the eye open for 9 to 11 seconds), the processing unit 120 determines that the blink code PUC of the user matches the preset unlock password and unlocks the located state of the security equipment 130.

On the other hand, when obtaining a blink code PUC' formed by a code sequence of "110111011110" based on the eye movements of the user, the processing unit 120 calculates the maximum time length COT of the first code B1 continuously appearing in the blink code PUC'. In the blink code PUC', the processing unit 120 calculates that the maximum time length COT of the first code B1 continuously appearing is about 4 unit time UT. When the maximum time length COT' is beyond the range from 9 to 11 seconds, the processing unit 120 determines that the blink code PUC' of the user does not match the preset unlock password and maintains the security equipment 130 in the locked state.

Herein, the preset eye-open time range (9 to 11 seconds) is only an example for illustration and construes no limitations to the invention. Furthermore, upper and lower limits of the eye-open time range may be selected by the designer, or alternatively, only the lower limit of the eye-open time range is set without the upper limit (i.e., as long as the user keeps the eye open over the lower limit of the set eye-open time range, it is determined that the corresponding blink code matches the preset unlock password).

Figure 6D:
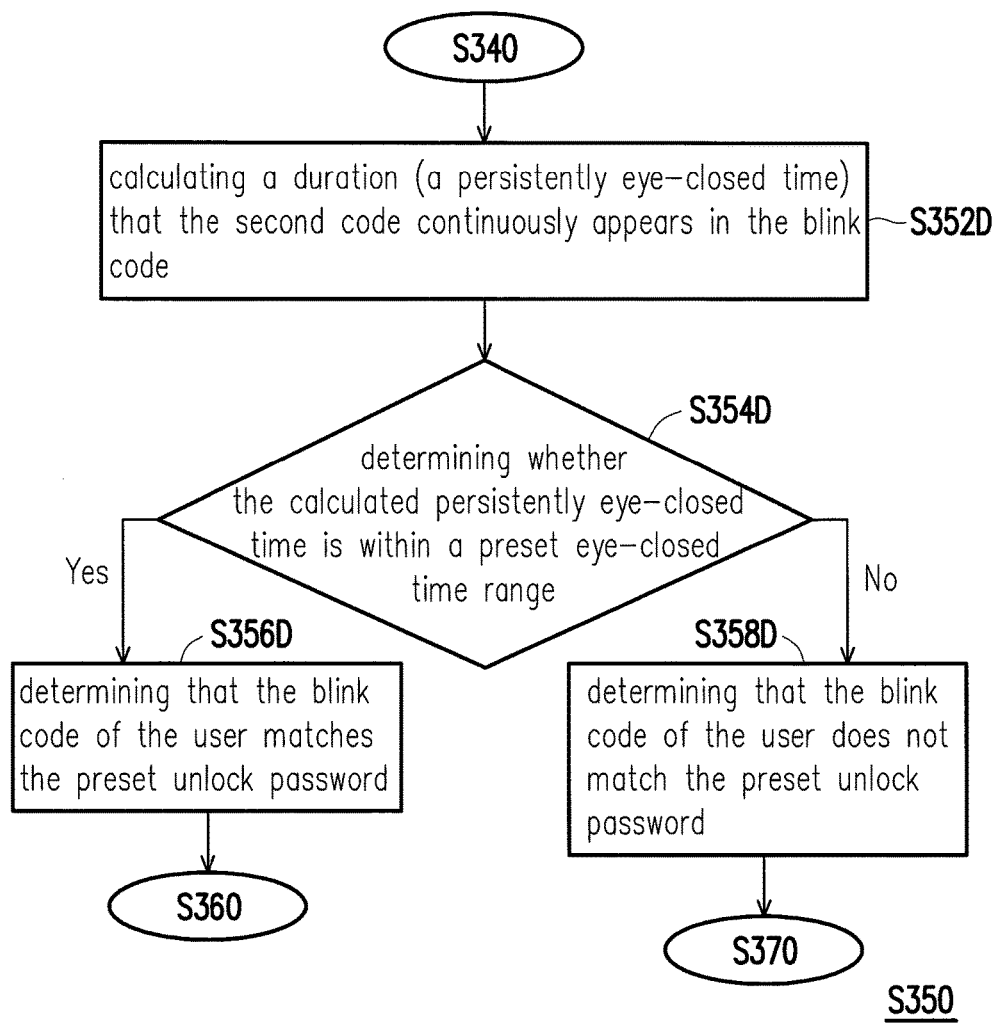

Referring to FIG. 6D, in the present embodiment, the preset unlock password is set to be a specific persistently eye-closed time. Specifically, in step S350 of the present embodiment, the processing unit 120 calculates a duration (i.e., a persistently eye-closed time) that the second code corresponding to the eye-closed state continuously appears in the blink code (step S352D). Then, the processing unit 120 determines whether the calculated persistently eye-closed time is within a preset eye-closed time range (step S354D). If determining that the persistently eye-closed time is within the preset eye-closed time range, the processing unit 120 determines that the blink code of the user matches preset unlock password (step S356D) and continues to perform step S360 of unlocking the located state of the security equipment 130. Otherwise, if determining that the persistently eye-closed time is beyond the preset eye-closed time range, the processing unit 120 determines that the blink code of the user does not match preset unlock password (step S358D) and continues to perform step S370 to maintain the security equipment 130 in the locked state.

Figure 7D:
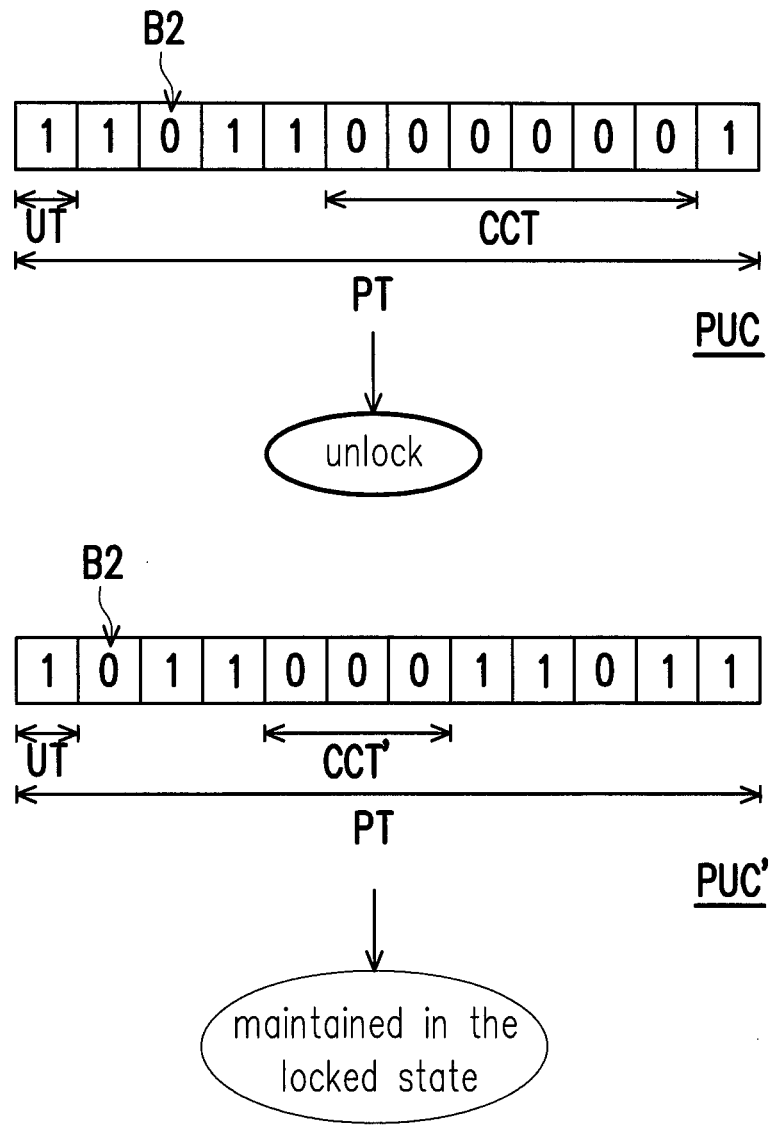

For instance, referring to FIG. 6D and FIG. 7D together, it is assumed that the preset eye-closed time range is set to range from 9 to 11 seconds. When obtaining a blink code PUC formed by a code sequence of "110110000001" based on the eye movements of the user, the processing unit 120 calculates a maximum time length CCT that the second code B2 (labeled as "0") continuously appears in the blink code PUC. In the blink code PUC, the processing unit 120 calculates that the maximum time length CCT of the second code B2 continuously appearing is about 6 unit time UT. When determining that the maximum time length CCT is within a range from 9 to 11 seconds (i.e., the user keeps the eye closed for 9 to 11 seconds), the processing unit 120 determines that the blink code PUC of the user matches the preset unlock password and unlocks the located state of the security equipment 130.

On the other hand, when obtaining a blink code PUC' formed by a code sequence of "101100011011" based on the eye movements of the user, the processing unit 120 calculates the maximum time length CCT' of the second code B2 continuously appearing in blink code PUC'. In the blink code PUC', the processing unit 120 calculates that the maximum time length CCT' of the second code B2 continuously appearing is about 3 unit time UT. When the maximum time length CCT' is beyond the range from 9 to 11 seconds, the processing unit 120 determines that the blink code PUC' of the user does not match the preset unlock password and maintains the security equipment 130 in the locked state.

Herein, the preset eye-closed time range (i.e., from 9 to 11 seconds) is only an example for illustration and construes no limitations to the invention. Furthermore, upper and lower limits of the eye-closed time range may be selected by the designer, or alternatively, only the lower limit of the eye-closed time range is set without the upper limit (i.e., as long as the user keeps the eye closed over the lower limit of the set eye-closed time range, it is determined that the corresponding blink code matches the preset unlock password).

Figure 6E:
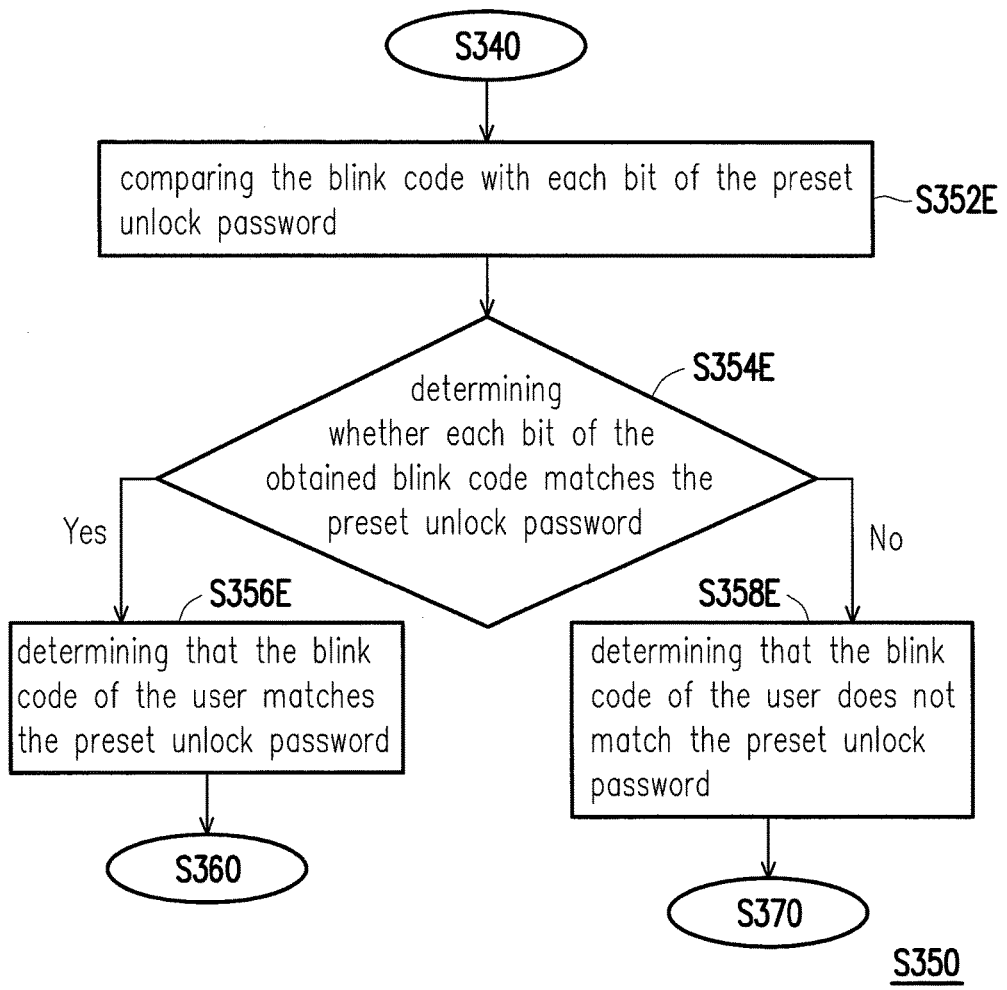

Referring to FIG. 6E, in the present embodiment, the processing unit 120 decides whether to unlock according to a comparison result whether the blink code is identical to the preset unlock password. Specifically, in step S350 of the present embodiment, the processing unit 120 compares the blink code with each bit of the preset unlock password (step S352E). Then, the processing unit 120 determines whether each bit of the obtained blink code matches the preset unlock password (step S354E). If it is determined that each bit of the blink code matches the preset unlock password, the processing unit 120 that the blink code of the user matches the preset unlock password (step S356E) and continues to perform step S360 to unlock the located state of the security equipment 130. Otherwise, if it is determined that at least one bit of the blink code does not match the preset unlock password, the processing unit 120 determines that the blink code of the user does not match the preset unlock password (step S358E) and continues to perform step S370 to maintain the security equipment 130 in the locked state.

Figure 7E:
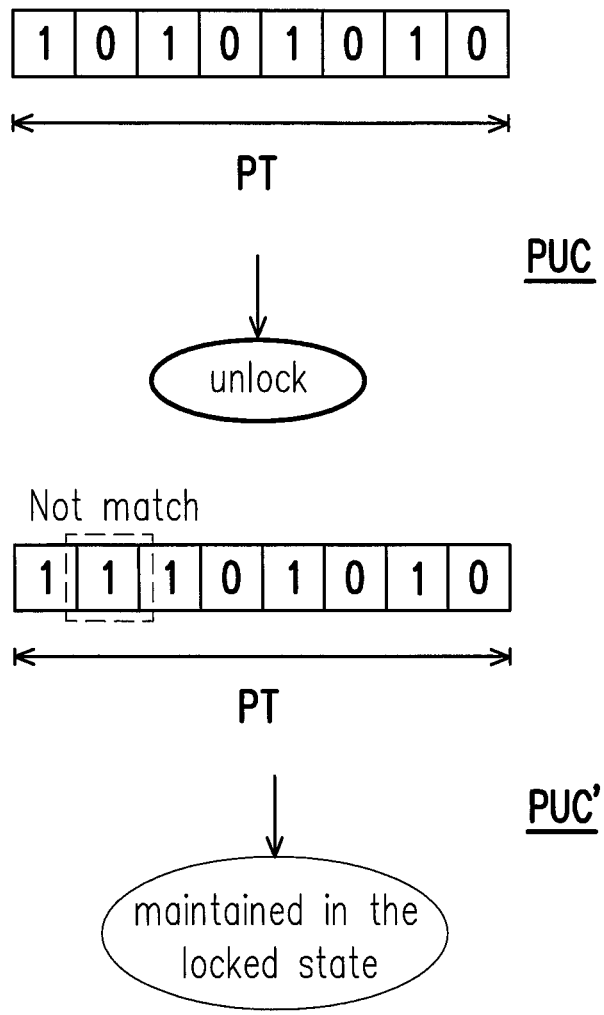

For instance, referring to FIG. 6E and FIG. 7E together, it is assumed that the preset unlock password is set to be an 8-bit code sequence formed by "10101010". When obtaining a blink code PUC formed by the code sequence of "10101010" based on the eye movements of the user, the processing unit 120 compares each bit of the obtained blink code PUC with the preset unlock password. After the comparison, the processing unit 120 determines that the blink code PUC of the user matches each bit of the preset unlock password, such that the processing unit 120 determines that the blink code PUC of the user matches the preset unlock password and unlocks the located state of the security equipment 130.

On the other hand, when obtaining a blink code PUC' formed by a code sequence of "11101010" based on the eye movements of the user, the processing unit 120 compares each bit of the obtained blink code PUC' with the preset unlock password. After the comparison, the processing unit 120 determines that the second bit of the blink code PUC' of the user does not match the preset unlock password, and thus, determines that the blink code PUC' of the user does not match the preset unlock password and maintains the security equipment 130 in the locked state.

Additionally, it should be mentioned that in the password inputting method of the present embodiment, step S350 of determining whether the blink code matches the preset unlock password is not limited to the implementation by solely adopting one of the examples illustrated in FIG. 6A to FIG. 6E, and the method may be implemented by collectively adopting at least two of the examples illustrated in FIG. 6A to FIG. 6D so as to simultaneously include at least two determination conditions for the blink number, the blink frequency, the persistently eye-open time, the persistently eye-closed time, which serve as the preset unlock password.

For instance, the designer may set the preset unlock password to be 3 times of continuous blinks (i.e., the preset blink number is equal to 3) first followed by an eye-closed action persisting for 9 to 11 seconds (i.e., the preset eye-closed time range is from 9 to 11 seconds). Herein, if obtaining a blink code in a format of "101010000000", the processing unit 120 may determine that the blink code matches the preset unlock password. In other words, under the preset unlock password, the user has to blink for 3 times (corresponding to 3 blink codes of "10") and then, keeps the eye closed for 9 to 11 seconds (corresponding to 6 second codes of "0"), such that the processing unit 120 would determine that the blink code of the user matches the preset unlock password. Here, the aforementioned condition is an example for illustrative convenience, and the invention is not limited thereto. Moreover, any combinations using the conditions including the blink number, the blink frequency, the persistently eye-open time and the persistently eye-closed time fall within the scope of the invention.

Figure 8:
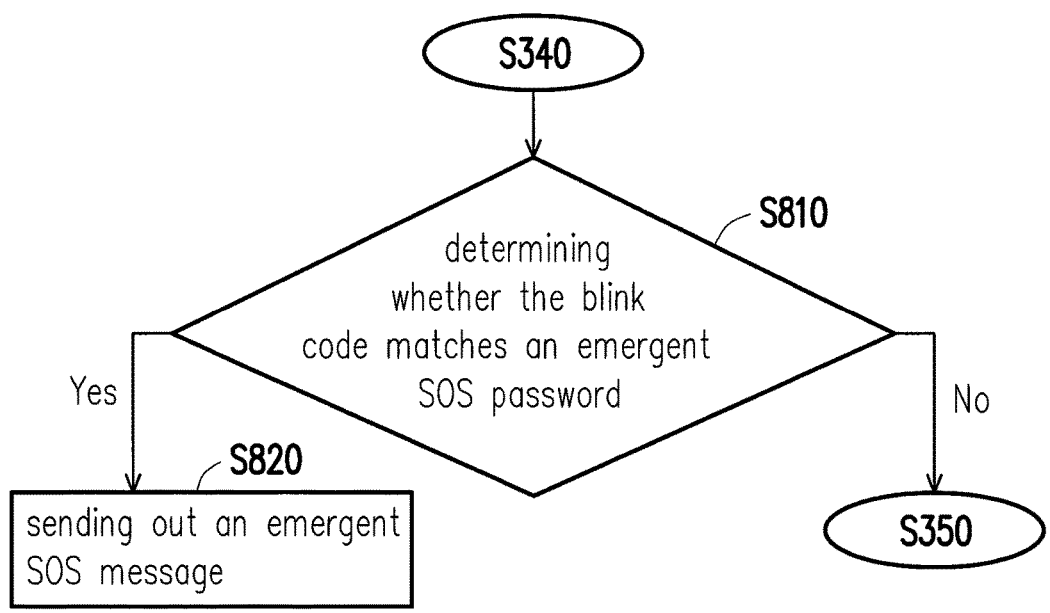
FIG. 8 is a flowchart illustrating a step of determining whether an emergency occurs according to an embodiment of the invention.

In addition to the process of unlocking based on the eye open and closed state, the invention further provides a password inputting method for determining whether an emergency of the user occurs, and the specific process flow is illustrated in FIG. 8.

FIG. 8 is a flowchart illustrating a step of determining whether an emergency occurs according to an embodiment of the invention. Referring to FIG. 8, in the present embodiment, before (or at the same time as, which is not limited in the invention) step S350 of determining whether the blink code of the user matches the preset unlock password, the password inputting method may determine whether the blink code of the user matches an emergent SOS password (step S810). If determining that the blink code of the user matches the emergent SOS password, it indicates that the user may probably be in an emergent situation (e.g., the user may probably be kidnapped), and thus, in this case, the processing unit 120 sends out an emergent SOS message (step S820) to a security unit to inform that an abnormal event occurs. Otherwise, if determining that the blink code of the user does not match the emergent SOS password, step S350 of determining whether the blink code matches the preset unlock password is then performed.

Herein, the specific implementation with respect to the step of comparing the blink code of the user with the emergent SOS password may refer to the description related to the step of comparing the blink code with the preset unlock password (e.g., embodiments illustrated in FIG. 6A to FIG. 7E) and will not be repeatedly described hereinafter.

Figure 9A:
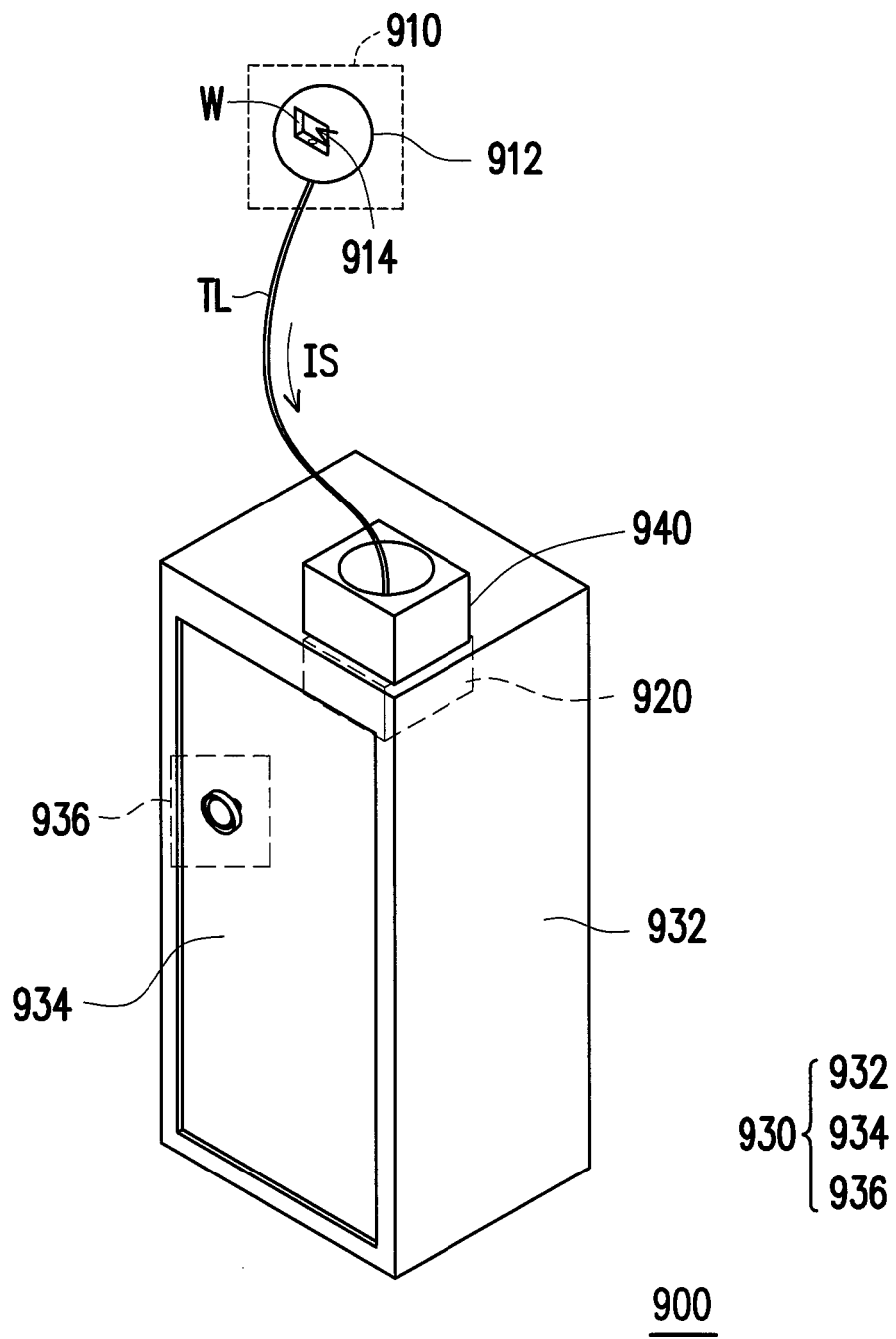
FIG. 9A is a schematic diagram illustrating an authentication system controlled by eye open and eye closed state according to an embodiment of the invention.
Figure 9B:
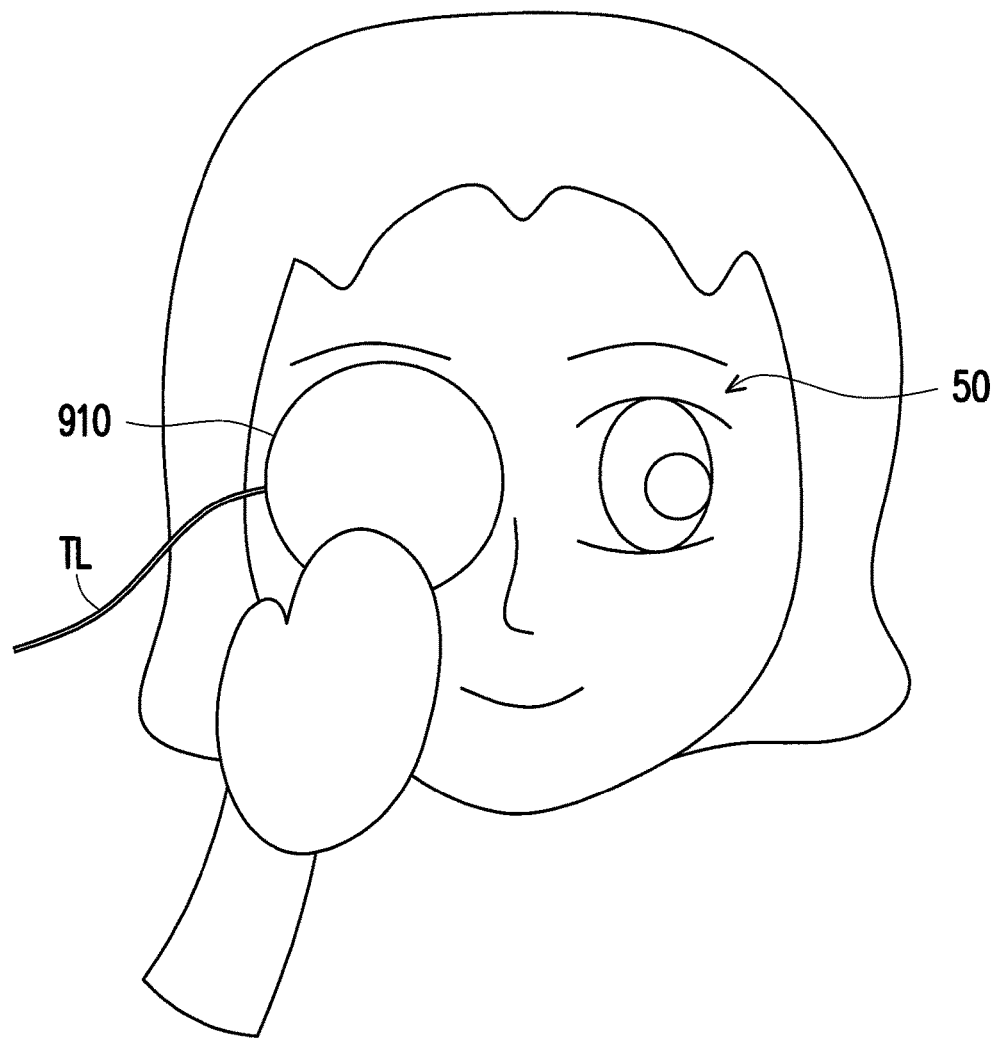
FIG. 9B is a schematic diagram for using the authentication system of an embodiment of FIG. 9A.

Examples of practical application of an authentication system controlled by eye open and eye closed state are described below with reference to embodiments of FIG. 9A to FIG. 10B. FIG. 9A is a schematic diagram illustrating an authentication system controlled by eye open and eye closed state according to an embodiment of the invention. FIG. 9B is a schematic diagram for using the authentication system of an embodiment of FIG. 9A.

Referring to FIG. 9, an authentication system 900 includes a handheld control apparatus 910, a processing unit 920, a security equipment 930 and a storage box 940. In the present embodiment, the security equipment 930 is, for example, a safety deposit box which includes a box body 932, a protection door 934 and lock 936. Interior of the box body 932 is a hollow design and includes an accommodating space for storing items. This accommodating space provides a space for storing various items such as precious jewelry, marketable securities, gold and so on. The protection door 934 is disposed on one side of the box body 932 and capable of moving in rotation. After being closed, the protection door 934 can cover the accommodating space of the box body 932, so that accommodating space is in a sealed state isolated from the outside and provides function of storing precious items. The lock 936 is disposed on the protection door 934, and configured to control opening or closing of the protection door 934.

When the lock 936 is controlled by the processing unit 920 to be in the locked state, the protection door 934 is locked onto the box body 932 and cannot be opened by the user. In contrary, when the lock 936 is controlled to be in the unlocked state, the protection door 934 can be opened by the user, so that the user may freely place the items into the accommodating space or get the items out of the accommodating space.

The handheld control apparatus 910 is movably disposed on an upper side of the box body 932 (but not limited thereto), and coupled to the processing unit 920 through a wired or wireless data transmission interface (even though a wired transmission interface that connects with a transmission line TL is illustrated in the present embodiment, the invention is not limited thereto). The handheld control apparatus 910 includes a housing case 912 and an image capturing unit 914. The housing case 912 has a window W and is suitable for a user to hold. The image capturing unit 914 is disposed in the housing case 912 and captures an eye area of the user through the window W to obtain an image sequence IS.

More specifically, as shown in FIG. 9B, when using the authentication system 900, the user may hold the handheld control apparatus 910 close to one eye, make the eye area align to the window W on the housing case 912, and perform the eye movements facing the window W for the image capturing unit 914 to capture the images of eye area of the user in order to obtain the image sequence IS. Then, the image capturing unit 914 transmits the obtained image sequence IS to the processing unit 920. Thereby, the processing unit 920 may determine whether the eye movements of the user match the preset unlock password according to aforesaid password inputting method, and decide whether to unlock the locked state of the lock. Therefore, the user may use the handheld control apparatus 910 to input the password more freely without restricted by location of the apparatus while avoiding peeping from someone else, so as to improve usage security of the authentication system 900.

In the present embodiment, the storage box 940 may be further disposed on the upper side of the box body 932 of the safety deposit box 930, and the storage box 940 provides a storage space for storing the handheld control apparatus 910 after the password is inputted by the user. In addition, in an exemplary embodiment, a reel (not illustrated) may be disposed inside the storage box 940, and the reel is capable of rewinding the transmission line TL so that the handheld control apparatus 910 may be stored inside the storage space.

Moreover, it should be mentioned that in the present embodiment, even though the processing unit 920 is disposed in the security equipment/the safety deposit box 930 for example, the invention is not limited thereto. In other exemplary embodiments, the processing unit 920 may also be directly disposed on the handheld control apparatus 910 (as another structure in the following embodiment of FIG. 10B). In this exemplary example, information transmitted from the handheld control apparatus 910 through the wired or wireless data transmission interface is the control command for switching the locked state of the security equipment/the safety deposit box 930.

Under the structure of the authentication system 900, the processing unit 920 may detect the eye movements made by the user according to the image sequence captured by the handheld control apparatus 910 by using the steps of the embodiments illustrated in FIG. 2 to FIG. 8, so as to determine whether the eye movements of the user match the preset unlock password. Then, whether to send a corresponding control signal to control the safety deposit box 930 to unlock the locked state may be decided according to the determination result, so that the user may open the protection door 934 in order to get the items out of the accommodating space or place the items into the accommodating space.

Figure 10A:
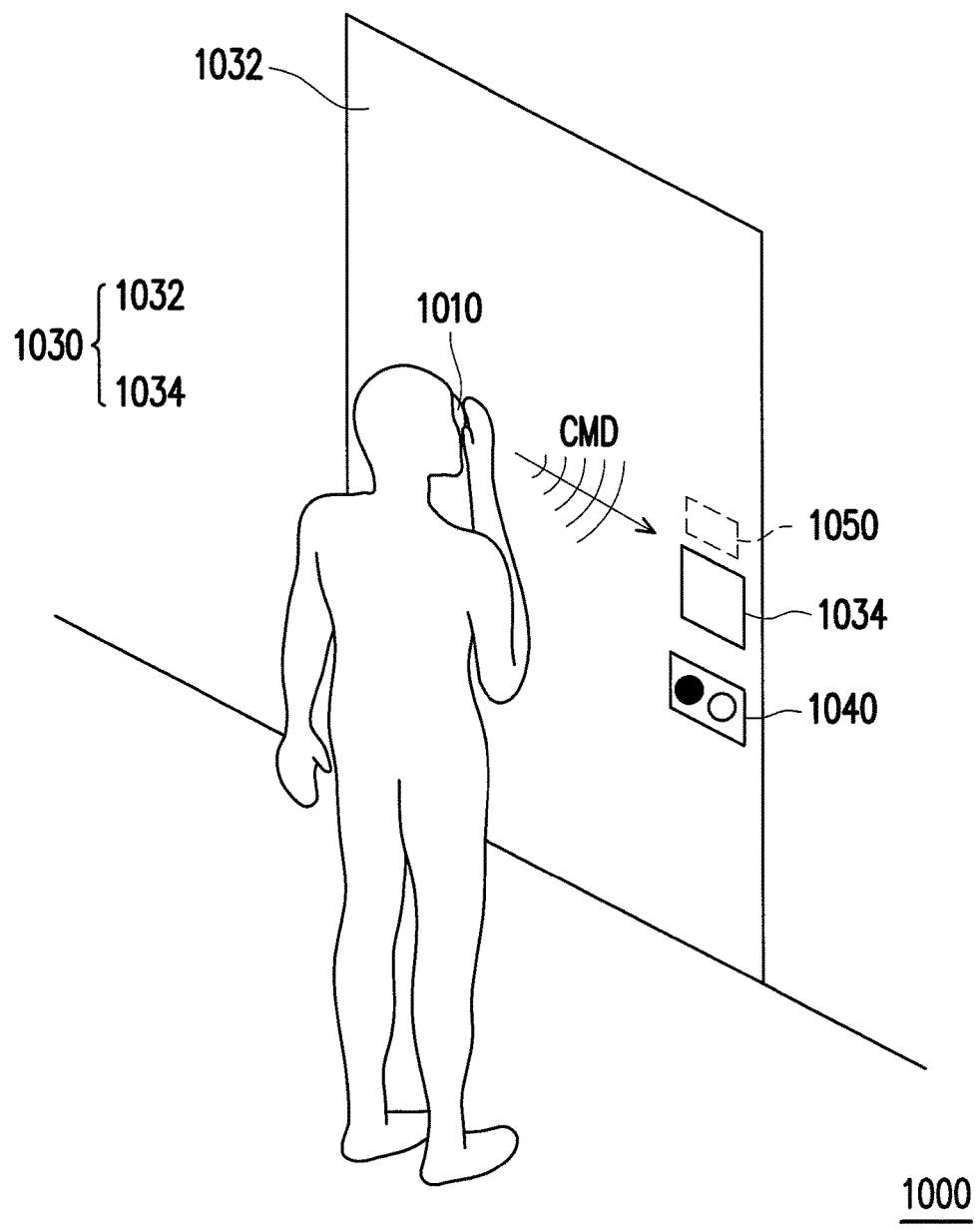
FIG. 10A is a schematic diagram illustrating an authentication system controlled by eye open and eye closed state according to another embodiment of the invention.
Figure 10B:
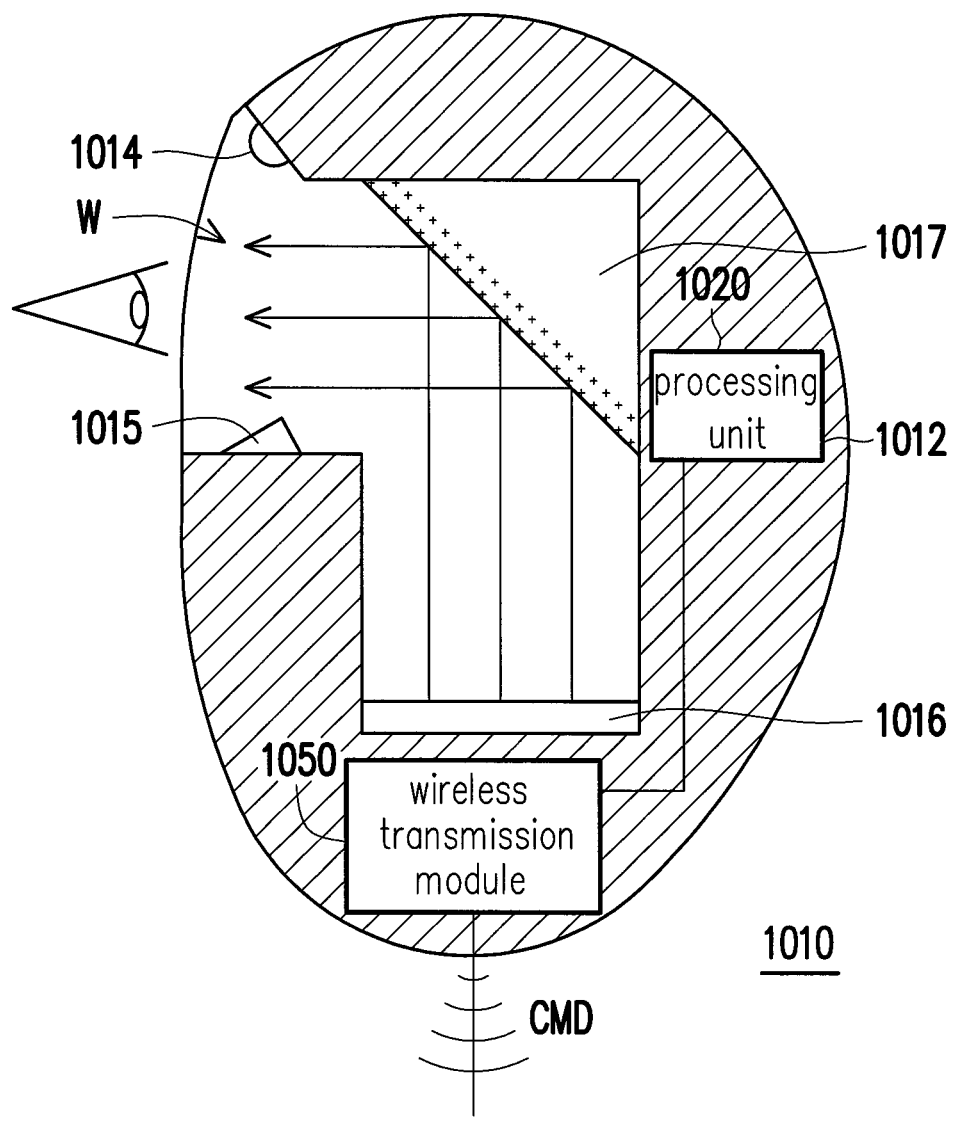
FIG. 10B and FIG. 10C are schematic diagrams illustrating applications of the handheld control apparatuses in different embodiments of FIG. 10A.
Figure 10C:
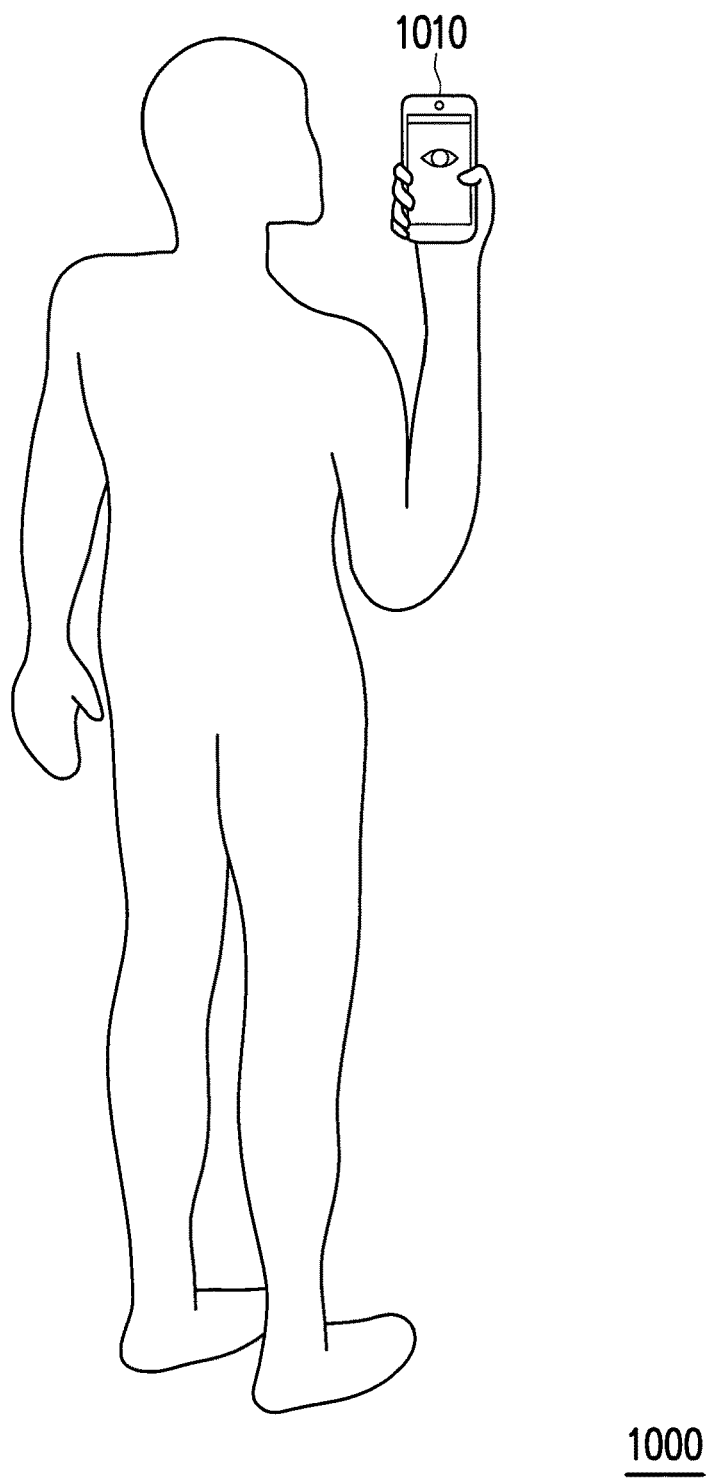

FIG. 10A is a schematic diagram illustrating an authentication system controlled by eye open and eye closed state according to another embodiment of the invention. FIG. 10B and FIG. 10C are schematic diagrams illustrating applications of the handheld control apparatuses of different embodiments of FIG. 10A.

Referring to FIG. 10A, an authentication system 1000 includes a handheld control apparatus 1010, a processing unit 1020, a security equipment 1030, a prompt unit 1040 and a wireless transmission module 1050. In the present embodiment, the processing unit 1020 is disposed in the handheld control apparatus 1010 for example, but the invention is not limited thereto.

The security equipment 1030 is, for example, an access control system which includes a door 1032 and a lock 1034. The lock 1034 is disposed on the door 1032, and configured to control opening or closing of the door 1032. The prompt unit 1040 in the present embodiment is, for example, a light indication apparatus serving to prompt whether a current configuration state of the lock 1034 is the locked state or the unlocked state by using light signals, but the invention is not limited thereto.

The wireless transmission module 1050 may include two transceiving terminals which are disposed on the security equipment/the access control system 1030 and the handheld control apparatus 1010 respectively, so as to provide a wireless data transmission interface (e.g., Short Distance Wireless Communication, Radio Frequency Identification (RFID), Bluetooth or Wi-Fi and etc.).

Specifically, when the user intends to use the authentication system 1000, the user may hold the handheld control apparatus 1010 close to the eye, and performs the eye movements facing the handheld control apparatus 1010. The handheld control apparatus 1010 captures the eye images of the user to generate the image sequence IS. The processing unit 1020 processes the captured image sequence IS and generate the control command CMD that instructs whether to unlock the locked state of the lock 1034 by using the steps illustrated in the embodiments of FIG. 2 to FIG. 6E. Then, the control command CMD is transmitted to the lock 1034 through the wireless transmission module 1050, so that lock 1034 may decide whether to unlock the locked state in response to the control command CMD.

FIG. 10B is an example of practical application of an embodiment of the handheld control apparatus 1010. Referring to FIG. 10B, the handheld control apparatus 1010 includes, for example, a housing case 1012, an image capturing unit 1014, a light source 1015, a display unit 1016 and a reflective mirror 1017. Further, the processing unit 1020 and one of the transceiving terminals of the wireless transmission module 1050 are also disposed in the handheld control apparatus 1010.

In the present embodiment, the housing case 1012 has a window W and is suitable for a user to hold. The image capturing unit 1014 and the light source 1015 are disposed in the housing case and adjacent to the window W. The light source 1015 may be turned on when the image capturing unit 1014 is capturing eye images of the user (or when the user approaches, and the invention is not limited thereto), so as to provide sufficient brightness. The display unit 1016 is disposed in the housing case 1012, and configured to display an image related to operating information; and the reflective minor 1017 is capable of reflecting the image of the operating information to the window W, so that user is able to view contents of the image displayed by the display unit 1016. Here, the operating information may be, for example, text that prompts the user to start perform the eye movements (such as "please input the password"), or text that indicates whether the password inputted by the user is correct, which construe no limitations to the invention.

Moreover, it should be mentioned that in the present embodiment, even though the processing unit 1020 is disposed on the handheld control apparatus 1010 for example, the invention is not limited thereto. In other exemplary embodiments, the processing unit 1020 may also be directly disposed in the security equipment/the safety deposit box 1030 (as the structure in the foregoing embodiment of FIG. 9A). In this exemplary example, information transmitted from the handheld control apparatus 1010 through the wired or wireless data transmission interface is the image sequence related to the eye area of the user.

FIG. 10C is an example of practical application of another embodiment of the handheld control apparatus 1010. Referring to FIG. 10C, in the present embodiment, the functions of the handheld control apparatus 1010 may be realized in a manner of software on a common smart phone. The function of capturing image by the handheld control apparatus 1010 may be realized by a camera module built-in the smart phone. The function of displaying the image related to the operating information may be realized by a display screen of the smart phone. When the smart phone is used as the handheld control apparatus 1010, the user may hold the smart phone and place the smart phone at a position with a specific working distance away from the eye of the user, so that a lens of the smart phone may focus on the eye of the user for capturing the eye movements of the user.

The above-described authentication method for the authentication system according to the present invention can be implemented in either hardware, firmware, or software or computer code that can be stored in a non-transitory computer readable recording medium, or computer code stored on a non-transient machine-readable medium such that the method described herein may be implemented in software that uses a general purpose computer or a specialized processor or a programmable or specialized hardware (such as an ASIC Or FPGA). However, the non-transitory computer readable recording media comprise all computer-readable media (such as a CD-ROM, RAM, floppy disk, hard disk or magneto-optical disk), with the sole exception being a transitory, propagating signal. It should be understood by those of ordinary skill in the art that a computer, processor, microprocessor controller, or programmable hardware includes storage elements (e.g., RAM, ROM, flash memory, etc.) that can store or receive software or computer code). The processor or hardware of an electronic device implements the processing method described herein when the software or computer code is accessed and executed by the electronic device. In addition, it should be noted that, when the general computer accesses the code for implementing the processing described herein, execution of the code transforms the general purpose computer into a dedicated computer for executing the processing described herein.

In summary, the authentication system controlled by eye open and eye closed state and the handheld control apparatus thereof are provided according to the embodiments of the invention. The authentication system may utilize a specific eye movements (e.g., blanking, persistently eye-opening and/or persistently eye-closing) as the unlock password for unlocking the locked state of the lock. Due to the eye movements of the user being difficulty peeped or observed by others, security equipments (e.g., access control systems or safety deposit boxes) applying the authentication system can be significantly advanced in security, and passwords therefore can be prevented from being leaked.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims and their equivalents.

What is claimed is:

1. A handheld control apparatus coupled to a security equipment and performing an authentication for a user, the apparatus comprising:
a housing case having a window;
an image capturing unit disposed within the housing case to capture a plurality of images of an eye area of the user through the window to obtain an image sequence, wherein the images of the image sequence are captured within a preset time period, the preset time period comprises a plurality of unit time periods sequentially connected in an order, and each of parts of the images are captured within each of the unit time periods; and
a processing unit coupled to the image capturing unit and configured to analyze the image sequence to obtain eye image information of the eye area in the image sequence,
wherein the processing unit sequentially detects whether a state of each of the images of the image sequences is an eye-open state or an eye-closed state based on the eye image information,
wherein the processing unit sequentially generates a plurality of codes of a code sequence through the detected states of the images of the image sequences, wherein the codes comprises one or more first codes and one or more second codes, and,
after the operation of generating the codes of the code sequence is complete, the processing unit generates a control command to control the security equipment according to the entire code sequence,
wherein in the operation of the processing unit sequentially generates the plurality of codes of the code sequence through the detected statuses of the images of the image sequences:
based on the order of the unit time periods, the processing unit sequentially generates one of the codes corresponding one of the unit time periods according to the states of images within the one of the unit time periods,
wherein when the states of images within one of the unit time periods are detected as the eye-open states, the processing unit generates one first code as one code corresponding to the one of the unit time periods, wherein the first code is a bit value,
wherein when the states of images within one of the unit time periods are detected as the eye-closed states, the processing unit generates one second code as one code corresponding to the one of the unit time periods, wherein the second code is another bit value different from the bit value of the first code,
wherein the generated first codes and the second codes are arranged in the order of the unit time periods to form the code sequence.

2. The handheld control apparatus of claim 1, further comprising:
a light source disposed in the housing case and adjacent to the window;
a display unit disposed in the housing case and configured to display operating information; and
a reflective mirror disposed in the housing case and reflecting an image of the operating information to the window.

3. The handheld control apparatus of claim 1, wherein the security equipment comprises a safety deposit box, an access control system or a network authentication system.

4. The handheld control apparatus of claim 1, further comprising:
a wireless transmission module configured to wirelessly transmit the control command to the security equipment.

5. The handheld control apparatus of claim 1, wherein the security equipment unlocks a locked state according to the control command when the processing unit determines that the code sequence matches a preset unlock password, wherein the security equipment is maintained in the locked state according to the control command when the processing unit determines that the code sequence does not match the preset unlock password.

6. The handheld control apparatus of claim 1, wherein the processing unit searches an eye object in the eye area based on the eye image information, and determines whether the eye area is in the eye-open state or the eye-closed state according to a size of the eye object.

7. The handheld control apparatus of claim 6, wherein the processing unit determines that the eye area is under the eye-closed state when a height of the eye object is less than a height threshold and a width of the eye object is greater than a width threshold; and wherein the processing unit determines that the eye area is under the eye-open state when the height of the eye object is greater than or equal to the height threshold, or the width of the eye object is less than or equal to the width threshold.

8. The handheld control apparatus of claim 6, wherein after the eye object is searched, the processing unit recognizes biometric information of the eye object; wherein when the biometric information matches preset user information, the processing unit determines whether the eye area is under the eye-open state or the eye-closed state according to the size of the eye object.

9. The handheld control apparatus of claim 1, wherein the processing unit defines the continuously generated first and second codes as the code sequence, counts a blink number of the code sequence appearing in the code sequence and compares the blink number with a preset blink number, determines that the code sequence matches a preset unlock password when the blink number is equal to the preset blink number, and determines that the code sequence does not match the preset unlock password when the blink number is unequal to the preset blink number.

10. The handheld control apparatus of claim 1, wherein the processing unit defines the continuously generated first and second codes as the code sequence, calculates a blink frequency of the code sequence appearing in the code sequence and determines whether the blink frequency is within a preset blink frequency range, determines that the code sequence matches a preset unlock password when the blink frequency is within the preset blink frequency range, and determines that the code sequence does not match the preset unlock password when the blink frequency is beyond the preset blink frequency range.

11. The handheld control apparatus of claim 1, wherein the processing unit calculates a persistently eye-open time of the first code continuously appearing in the code sequence and determines whether the persistently eye-open time is within a preset eye-open time range, determines that the code sequence matches a preset unlock password when the persistently eye-open time is within the preset eye-open time range, and determines that the code sequence does not match the preset unlock password when the persistently eye-open time is beyond the preset eye-open time range.

12. The handheld control apparatus of claim 1, wherein the processing unit calculates a persistently eye-closed time of the second code continuously appearing in the code sequence and determines whether the persistently eye-closed time is within a preset eye-closed time range, determines that the code sequence matches a preset unlock password when the persistently eye-closed time is within the preset eye-closed time range, and determines that the code sequence does not match the preset unlock password when the persistently eye-closed time is beyond the preset eye-closed time range.

13. The handheld control apparatus of claim 1, wherein the processing unit compares the code sequence with each bit of a preset unlock password, determines that the code sequence matches the preset unlock password when each bit of the code sequence matches the preset unlock password, and determines that the code sequence does not match the preset unlock password when at least one bit in the code sequence does not match the preset unlock password.

14. The handheld control apparatus of claim 1, wherein the processing unit further determines whether the code sequence matches an emergent SOS password, and sends out an emergent SOS message when the code sequence matches the emergent SOS password.

15. An authentication system, comprising:
a handheld control apparatus configured to capture a plurality of images of an eye area of a user to obtain an image sequence, wherein the images of the image sequence are captured within a preset time period, the preset time period comprises a plurality of unit time periods sequentially connected in an order, and each of parts of the images are captured within each of the unit time periods;
a processing unit for receiving and analyzing the image sequence from the handheld control apparatus through a data transmission interface to obtain eye image information of the eye area in the image sequence; and
a security equipment coupled to the processing unit for switching a locked state according to a control command;

wherein the processing unit sequentially detects whether a state of each of the images of the image sequences is an eye-open state or an eye-closed state based on the eye image information,
wherein the processing unit sequentially generates a plurality of codes of a code sequence through the detected states of the images of the image sequences, wherein the codes comprises one or more first codes and one or more second codes, and
after the operation of generating the codes of the code sequence is complete, the processing unit generates the control command according to the entire code sequence,
wherein in the operation of the processing unit sequentially generates the plurality of codes of the code sequence through the detected statuses of the images of the image sequences:
based on the order of the unit time periods, the processing unit sequentially generates one of the codes corresponding one of the unit time periods according to the states of images within the one of the unit time periods,
wherein when the states of images within one of the unit time periods are detected as the eye-open states, the processing unit generates one first code as one code corresponding to the one of the unit time periods, wherein the first code is a bit value,
wherein when the states of images within one of the unit time periods are detected as the eye-closed states, the processing unit generates one second code as one code corresponding to the one of the unit time periods, wherein the second code is another bit value different from the bit value of the first code,
wherein the generated first codes and the second codes are arranged in the order of the unit time periods to form the code sequence.

16. The authentication system controlled by eye open and eye closed state of claim 15, wherein the handheld control apparatus comprises:
a housing case, having a window, wherein the housing case is suitable for the user to hold; and
an image capturing unit, disposed in the housing case, and capturing the eye area of the user through the window to obtain the image sequence.

17. The authentication system controlled by eye open and eye closed state of claim 15, wherein the handheld control apparatus comprises:
a light source, disposed in the housing case, and adjacent to the window;
a display unit, disposed in the housing case, and configured to display operating information; and
a reflective mirror, disposed in the housing case, and reflecting an image of the operating information to the window.

18. The authentication system controlled by eye open and eye closed state of claim 15, wherein the data transmission interface comprises a wireless transmission module.

19. A non-transitory computer readable recording media for storing a program which executes an authentication method for a user by a handheld control apparatus coupled to a security equipment, the handheld control apparatus includes a housing case and an image capturing unit, the authentication method includes:
capturing, by the image capturing unit, a plurality of images of an eye area of the user through a window of the housing case to obtain an image sequence, wherein the images of the image sequence are captured within a preset time period, the preset time period comprises a plurality of unit time periods sequentially connected in an order, and each of parts of the images are captured within each of the unit time periods;

analyzing the image sequence to obtain eye image information of the eye area in the image sequence;

sequentially detecting whether a state of each of the images of the image sequences is an eye-open state or an eye-closed state based on the eye image information;

sequentially generating a plurality of codes of a code sequence through the detected states of the images of the image sequences, wherein the codes comprises one or more first codes and one or more second codes; and after the operation of generating the codes of the code sequence is complete, generating a control command to control the security equipment according to the entire code sequence, wherein the step of sequentially generating the plurality of codes of the code sequence through the detected statuses of the images of the image sequences comprises:

based on the order of the unit time periods, sequentially generating one of the codes corresponding one of the unit time periods according to the states of images within the one of the unit time periods, wherein when the states of images within one of the unit time periods are detected as the eye-open states, generating one first code as one code corresponding to the one of the unit time periods, wherein the first code is a bit value, wherein when the states of images within one of the unit time periods are detected as the eye-closed states, generating one second code as one code corresponding to the one of the unit time periods, wherein the second code is another bit value different from the bit value of the first code, wherein the generated first codes and the second codes are arranged in the order of the unit time periods to form the code sequence.

* * * * *